US010221451B2

(12) United States Patent
Hinz et al.

(10) Patent No.: US 10,221,451 B2
(45) Date of Patent: Mar. 5, 2019

(54) IMMOBILIZED BUFFER PARTICLES AND USES THEREOF

(71) Applicant: LIFE TECHNOLOGIES CORPORATION, Carlsbad, CA (US)

(72) Inventors: Wolfgang Hinz, Killingworth, CT (US); David Light, New Haven, CT (US); Todd Rearick, Cheshire, CT (US); James A. Ball, Ledyard, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 533 days.

(21) Appl. No.: 14/754,231

(22) Filed: Jun. 29, 2015

(65) Prior Publication Data

US 2015/0299787 A1    Oct. 22, 2015

Related U.S. Application Data

(63) Continuation of application No. 13/172,048, filed on Jun. 29, 2011, now abandoned.

(60) Provisional application No. 61/502,197, filed on Jun. 28, 2011, provisional application No. 61/359,790, filed on Jun. 29, 2010.

(51) Int. Cl.
*C12Q 1/6874* (2018.01)
*G01N 27/414* (2006.01)

(52) U.S. Cl.
CPC ....... *C12Q 1/6874* (2013.01); *G01N 27/4145* (2013.01)

(58) Field of Classification Search
CPC ......... B01D 2325/26; B01L 2200/0668; B01L 2300/0636; B01L 2300/0819; B01L 2300/0877; B01L 3/502761; G01N 27/4148; G01N 27/44717; G01N 27/4145; G01N 27/04; C12Q 1/6869; C12Q 2527/119; C12Q 2533/101; C12Q 2565/607; C12Q 1/6874
See application file for complete search history.

(56) References Cited

U.S. PATENT DOCUMENTS

| 5,766,934 | A | 6/1998 | Guiseppi-Elie | |
|---|---|---|---|---|
| 6,602,702 | B1 | 8/2003 | McDevitt et al. | |
| 2002/0094533 | A1* | 7/2002 | Hess | B01J 19/0046 435/6.14 |
| 2004/0040851 | A1 | 3/2004 | Karger et al. | |
| 2008/0032295 | A1* | 2/2008 | Toumazou | C12Q 1/6825 435/6.11 |
| 2008/0166727 | A1 | 7/2008 | Esfandyarpour et al. | |
| 2009/0127589 | A1* | 5/2009 | Rothberg | C12Q 1/6874 257/253 |
| 2010/0005959 | A1* | 1/2010 | Littau | B01D 53/228 95/51 |

(Continued)

OTHER PUBLICATIONS

Al-Kaysi, Rabih et al., "Effects of Sonication on the Size and Crystallinity of Stable Zwitterionic Organic Nanoparticles Formed by Reprecipitation in Water", *Langmuir*, 21, 2005, 7990-7994.

(Continued)

*Primary Examiner* — Sally A Merkling

(57) ABSTRACT

The disclosure relates to novel particle compositions and methods of making said compositions having applications in nucleic acid analysis, as well as apparatuses and systems for the same.

20 Claims, 8 Drawing Sheets

(56) References Cited

U.S. PATENT DOCUMENTS

2011/0003343 A1    1/2011    Nikiforov et al.

OTHER PUBLICATIONS

EP11834771-5, "Extended European Search Report dated Jan. 21, 2014", 5 pages.
PCT/US2011/042241, "International Preliminary Report on Patentability dated Jan. 17, 2013".
PCT/US2011/042241, "International Search Report dated Jan. 11, 2012".
PCT/US2011/042241, "Written Opinion of the International Searching Authority dated Jan. 11, 2012".

* cited by examiner

IMMOBILIZED BUFFER PARTICLES AND USES THEREOF

This application is a Continuation Application of U.S. patent application Ser. No. 13/172,048, filed Jun. 29, 2011 which claims priority to U.S. Provisional Application No. 61/359,790, filed Jun. 29, 2010, and U.S. Provisional Application No. 61/502,197, filed Jun. 28, 2011, which applications are incorporated by reference herein in their entireties.

In some embodiments, the disclosure relates generally to novel particle compositions and methods of making said compositions having applications in nucleic acid analysis, as well as apparatuses and systems for the same.

The development of ion-sensitive field-effective transistors (ISFETs) has led to the development of large-scale arrays of pH-sensitive sensors with applications in cell biology, environmental science, and genetic analysis. See, e.g., Yeow et al., *Sensors and Actuators* B 44: 434-440 (1997); Martinoia et al., *Biosensors & Bioelectronics*, 16: 1043-1050 (2001); Hammond et al., *IEEE Sensors J.*, 4: 706-712 (2004); Milgrew et al., *Sensors and Actuators* B 103; 37-42 (2004); Milgrew et al., *Sensors and Actuators* B, 111-112: 347-353 (2005); Hizawa et al., *Sensors and Actuators* B, 117: 5099-515 (2006); Heer et al., *Biosensors and Bioelectronics*, 22: 2546-2553 (2007; Barbaro et al., *Sensors and Actuators* B, 118: 41-46 (2006); Anderson et al., *Sensors and Actuators* B, 129: 79-86 (2008); Rothberg et al., U.S. Patent Publication No. 2009/0127589; Rothberg et al., U.K. Patent Application No. GB24611127; and the like. In particular, several of these applications involve the use of such large-scale arrays to monitor multiple reaction steps on a large plurality of analytes that are spatially confined, such as in a confinement region including, for example, in microwells or cavities on a sensor array surface. See, e.g., Anderson et al. (cited above); Rothberg et al. (cited above); and the like. Reactions taking place on such analytes may be monitored by one or more electronic sensors associated with each of the confinement regions. When the ionic signals being detected are weak, changes in the pH or ionic conditions of bulk reagents on an array can have an effect on chemical signals generated locally, thereby reducing signal-to-noise ratios.

In view of the above, it would be advantageous to have available compositions, methods, and systems for controlling conditions, such as pH, in bulk reagents, but which do not affect such conditions at local reactions in confinement regions.

In the following description, various aspects and embodiments of the disclosure will become evident. In its broadest sense, the disclosure could be practiced without having one or more features of these aspects and embodiments. Further, these aspects and embodiments are exemplary. Additional objects and advantages of the disclosure will be set forth in part in the description which follows, and in part will be obvious from the description, or may be learned by practicing the disclosure. The objects and advantages of the disclosure will be realized and attained by means of the elements and combinations particularly pointed out in the appended claims.

SUMMARY

In some embodiments, the disclosure relates generally to compositions, methods, and systems with applications in nucleic acid analysis, for example, for controlling pH in bulk reagents that are delivered to arrays of reactions confined to local regions, when transient pH values, or other physical or chemical properties such as heat or phosphate levels, are being measured in such local regions. In various aspects, the disclosure relates to immobilized buffer particles comprising one or more polymer networks and/or gels, such as a hydrogel, wherein one or more buffering groups are linked to the one or more polymer networks or gels.

In some embodiments, the disclosure provides compositions comprising immobilized buffer particles that are immersed in the bulk reagents, but that have sizes, shapes, and/or physical properties that preclude access to the confined local regions where reactions occur.

In some embodiments, the disclosure provides buffer compositions comprising an aqueous reagent; and a plurality of immobilized buffer particles contained therein, each particle having thereon one or more immobilized buffering groups. The buffering groups are typically linked to the polymer network or gel so as to prevent their separation from the network or gel in aqueous reagents, while the immobilized buffer particles themselves can typically move freely within such aqueous reagents.

As used herein, the term "immobilized" with regard to buffering particles is not intended to mean that the particles themselves are immobilized or not able to move about, but rather, to signal that the buffer itself is immobile. It should also be noted that the terms "immobilized buffer particles," "immobilized buffering particles," "buffer particles," "buffering particles," and "particles" are all used interchangeably herein, and are intended to signify the same thing.

In various exemplary embodiments, the one or more immobilized buffering groups may each have a known pKa, and therefore may be selected to buffer the aqueous reagent at a predetermined pH value. In further exemplary embodiments, the particles each have a size and the plurality of particles may optionally have a size distribution. In some embodiments, the size distribution of the plurality of particles has a coefficient of variation of less than about fifty percent, typically less about 40%, optionally less than about 30%, 20%, 15% or 10%. In some embodiments, the disclosure relates generally to an immobilized buffer particle comprising one or more polymer networks, wherein one or more buffering groups are linked to at least one of the one or more polymer networks.

In some embodiments, the disclosure relates generally to an immobilized buffer particle, wherein the polymer network comprises at least one polymer that is hydrophilic.

In some embodiments, the disclosure relates generally to an immobilized buffer particle, wherein the polymer network includes a network structure having one or more pores, wherein at least one of the one or more pores permits access to the interior of particle by solvents or reagents.

In some embodiments, the disclosure relates generally to an immobilized buffer particle, wherein the one or more buffering groups is selected from the group consisting of triethanolamine, N-[tris(hydroxymethyl) methyl]-2-aminoethanesulfonic acid, 3-(N-tris[hydroxymethyl]methylamino)-2-hydroxypropanesulfonic acid, N-(2-hydroxyethyl) piperazine-N-(2-ethanesulfonic acid), N-(2-acetamido)-2-aminoethanesulfonic acid, imidazole, and acetate.

In some embodiments, the disclosure relates generally to an immobilized buffer particle, wherein the one or more buffering groups is selected to have a pKa within the range of about 4.5 to about 9.0.

In some embodiments, the disclosure relates generally to an immobilized buffer particle, wherein the at least one or more immobilized buffering groups has a pKa in the range of about 6.0 to about 8.0.

In some embodiments, the disclosure relates generally to an immobilized buffer particle, wherein the immobilized buffer particle is an electrically charged particle.

In some embodiments, the disclosure relates generally to an immobilized buffer particle, wherein the electrically charged immobilized buffer particle is situated inside an apparatus for measuring pH values that includes a confinement region containing one or more zones of like polarity, and wherein the electrically charged particle has an electrical charge having the same polarity as the like charges contained in the one or more zones of the confinement region of the apparatus.

In some embodiments, the disclosure relates generally to an immobilized buffer particle, wherein the electrically charged immobilized buffer particle is situated inside an apparatus for detecting an analyte of interest that includes a confinement region containing one or more zones of like polarity, and wherein the electrically charged particle has an electrical charge having the same polarity as the like charges contained in the one or more zones of the confinement region of the apparatus.

In some embodiments, the disclosure relates generally to an immobilized buffer particle, wherein the immobilized buffer particle is situated inside an apparatus that includes a confinement region, wherein the immobilized buffer particle has a maximum length in any one dimension that is smaller than at least one diameter of the confinement region.

In some embodiments, the disclosure relates generally to an immobilized buffer particle, wherein the immobilized buffer particle is situated inside an apparatus that includes a confinement region, wherein the immobilized buffer particle has a minimum length in any one dimension that is greater than at least one diameter of the confinement region.

In some embodiments, the disclosure relates generally to an immobilized buffer particle, wherein the confinement region includes, or is associated with, a sensor for detecting an analyte of interest.

In some embodiments, the disclosure relates generally to an immobilized buffer particle, wherein the confinement region includes, or is associated with, a sensor for detecting the pH of a solution within the confinement region.

In some embodiments, the disclosure relates generally to an immobilized buffer particle comprising a gel, wherein one or more buffering groups are linked to the gel.

In some embodiments, the disclosure relates generally to an immobilized buffer particle comprising a gel, wherein the gel is made of polymers that are hydrophilic.

In some embodiments, the disclosure relates generally to an immobilized buffer particle comprising a gel, wherein the one or more buffering groups is selected from the group consisting of triethanolamine, N-[tris(hydroxymethyl) methyl]-2-aminoethanesulfonic acid, 3-(N-tris[hydroxymethyl]methylamino)-2-hydroxypropanesulfonic acid, N-(2-hydroxyethyl)piperazine-N-(2-ethanesulfonic acid), N-(2-acetamido)-2-aminoethanesulfonic acid, imidazole, and acetate.

In some embodiments, the disclosure relates generally to an immobilized buffer particle comprising a gel, wherein the one or more buffering groups is selected to have a pKa within the range of about 4.5 to about 9.0.

In some embodiments, the disclosure relates generally to an immobilized buffer particle comprising a gel, wherein the at least one or more immobilized buffering groups has a pKa in the range of about 6.0 to about 8.0.

In some embodiments, the disclosure relates generally to an immobilized buffer particle comprising a gel, wherein the immobilized buffer particle is an electrically charged particle.

In some embodiments, the disclosure relates generally to an immobilized buffer particle comprising a gel, wherein the electrically charged immobilized buffer particle is situated inside an apparatus for measuring pH values that includes a confinement region containing one or more zones of like polarity, and wherein the electrically charged particle has an electrical charge having the same polarity as the charges contained in the one or more zones of the confinement region of the apparatus.

In some embodiments, the disclosure relates generally to an immobilized buffer particle comprising a gel, wherein the electrically charged immobilized buffer particle is situated inside an apparatus for detecting an analyte of interest that includes a confinement region containing one or more zones of like polarity, and wherein the electrically charged particle has an electrical charge having the same polarity as the charges contained in the one or more zones of the confinement region of the apparatus.

In some embodiments, the disclosure relates generally to an immobilized buffer particle comprising a gel, wherein the immobilized buffer particle is situated inside an apparatus that includes a confinement region, wherein the immobilized buffer particle has a maximum length in any one dimension that is smaller than at least one diameter of the confinement region.

In some embodiments, the disclosure relates generally to an immobilized buffer particle comprising a gel, wherein the immobilized buffer particle is situated inside an apparatus that includes a confinement region, wherein the immobilized buffer particle has a minimum length in any one dimension that is greater than at least one diameter of the confinement region.

In some embodiments, the disclosure relates generally to an immobilized buffer particle comprising a gel, wherein the confinement region includes, or is associated with, a sensor for detecting an analyte of interest.

In some embodiments, the disclosure relates generally to an immobilized buffer particle comprising a gel, wherein the confinement region includes, or is associated with, a sensor for detecting the pH of a solution within the confinement region.

In some embodiments, the disclosure relates generally to a buffer composition comprising: an aqueous reagent; and a plurality of immobilized-buffer particles contained therein, wherein at least one particle includes a polymer network linked to one or more buffering groups, wherein at least one of the one or more buffering groups has a pKa within a predetermined range.

In some embodiments, the disclosure relates generally to a buffer composition, wherein at least one of the one or more buffering groups has a pKa in the range of about 4.5 to about 9.0.

In some embodiments, the disclosure relates generally to a buffer composition, wherein at least one of the one or more buffering groups has a pKa in the range of about 6.0 to about 8.0.

In some embodiments, the disclosure relates generally to a buffer composition, wherein at least one of the plurality of immobilized buffer particles has a size and wherein the plurality of immobilized buffer particles has a size distribution with a coefficient of variation of less than about 50%.

In some embodiments, the disclosure relates generally to a buffer composition, wherein the polymer network comprises at least one polymer that is hydrophilic.

In some embodiments, the disclosure relates generally to a buffer composition, wherein the polymer network includes a network structure having one or more pores, wherein at least one of the one or more pores permits access to the interior of particle by solvents or reagents.

In some embodiments, the disclosure relates generally to a buffer composition, wherein at least one of the one or more buffering groups is selected from the group consisting of triethanolamine, N-[tris(hydroxymethyl) methyl]-2-aminoethanesulfonic acid, 3-(N-tris[hydroxymethyl]methylamino)-2-hydroxypropanesulfonic acid, N-(2-hydroxyethyl) piperazine-N-(2-ethanesulfonic acid), N-(2-acetamido)-2-aminoethanesulfonic acid, imidazole, and acetate.

In some embodiments, the disclosure relates generally to a buffer composition, wherein at least one immobilized buffer particle of the plurality is an electrically charged particle.

In some embodiments, the disclosure relates generally to a buffer composition, wherein at least some portion of the buffer composition is situated inside an apparatus that includes a confinement region containing one or more zones of like charge, and wherein the electrically charged particle has an electrical charge having the same polarity as the charges contained in the one or more zones of the confinement region of the apparatus.

In some embodiments, the disclosure relates generally to a buffer composition, wherein at least some portion of the buffer composition is situated inside an apparatus that includes a confinement region, wherein the at least one immobilized buffer particle of the plurality has a maximum length in any one dimension that is smaller than at least one diameter of the confinement region.

In some embodiments, the disclosure relates generally to a buffer composition, wherein at least some portion of the buffer composition is situated inside an apparatus that includes a confinement region, wherein the at least one immobilized buffer particle of the plurality has a minimum length in any one dimension that is greater than at least one diameter of the confinement region.

In some embodiments, the disclosure relates generally to a buffer composition, wherein the confinement region includes, or is associated with, a sensor for detecting an analyte of interest.

In some embodiments, the disclosure relates generally to a buffer composition, wherein the confinement region includes, or is associated with, a sensor for detecting the pH of a solution within the confinement region.

In some embodiments, the disclosure relates generally to a buffer composition, wherein the buffer composition is situated inside an apparatus that includes a confinement region, wherein said aqueous reagent has a volume and wherein said plurality of particles has a concentration in said aqueous reagent so that said aqueous reagent has a substantially constant pH value throughout the volume except within the confinement region.

In some embodiments, the disclosure relates generally to a method of making an immobilized buffering polymer particle comprising the steps of: forming a reaction mixture comprising monomer, crosslinker and one or more types of buffering groups, and performing a polymerization reaction to produce a lot candidate immobilized buffer particle comprising one or more polymer networks, wherein one or more buffering groups are linked to at least one of the one or more polymer networks.

In some embodiments, the disclosure relates generally to a method of making an immobilized buffering polymer particle, wherein the performing further includes controlling the polymerization reaction by adjusting one or more physical conditions.

In some embodiments, the disclosure relates generally to a method of making an immobilized buffering polymer particle, wherein the one or more physical conditions is application of heat.

In some embodiments, the disclosure relates generally to a method of making an immobilized buffering polymer particle, wherein the one or more physical conditions is the addition of a catalyst.

In some embodiments, the disclosure relates generally to a method of making an immobilized buffering polymer particle, wherein the polymer network comprises at least one polymer that is hydrophilic.

In some embodiments, the disclosure relates generally to a method of making an immobilized buffering polymer particle, wherein the polymer network includes a network structure having one or more pores, wherein the at least one of the one or more pores permits access to the interior of particle for solvents or reagents.

In some embodiments, the disclosure relates generally to a method of making an immobilized buffering polymer particle, wherein the one or more buffering groups are linked to one or more chains of polymerized monomers within the polymer network.

In some embodiments, the disclosure relates generally to a method of making an immobilized buffering polymer particle, wherein the one or more buffering groups are linked to the immobilized buffer particle after the particle is formed through polymerization.

In some embodiments, the disclosure relates generally to a method of making an immobilized buffering polymer particle, further comprising the step of selecting candidate immobilized buffer particles in a predetermined size.

In some embodiments, the disclosure relates generally to a method of making an immobilized buffering polymer particle, wherein the performing further includes copolymerizing the buffering groups, monomers, and crosslinkers, thereby attaching the one or more buffering groups to at least one of the one or more polymer networks.

In some embodiments, the disclosure relates generally to a method of making an immobilized buffering polymer particle, wherein the shapes and size distributions of at least one of the one or more polymer networks of the immobilized buffer particle are further defined by a physical process.

In some embodiments, the disclosure relates generally to a method of making an immobilized buffering polymer particle, wherein the physical process may be any one of flow focusing using microfluidic devices; pneumatic disruption of a sheath-sample flow stream; sonication; controlled shearing; and membrane emulsion.

In some embodiments, the disclosure relates generally to a method of linking one or more buffering groups to a candidate immobilized buffer particle comprising the steps of selecting candidate particles in a predetermined size, and linking one or more buffering groups to at least one of the candidate particles, thereby forming at least one immobilized buffer particle.

In some embodiments, the disclosure relates generally to a method of linking one or more buffering groups to a candidate immobilized buffer particle, further comprising modifying the one or more buffering groups before the linking.

In some embodiments, the disclosure relates generally to a method of linking one or more buffering groups to a candidate immobilized buffer particle, further comprising modifying the one or more buffering groups after the linking.

In some embodiments, the disclosure relates generally to a method of linking one or more buffering groups to a candidate immobilized buffer particle, further comprising the step of attaching the one or more buffering groups to the immobilized buffer particle using click chemistry.

In some embodiments, the disclosure relates generally to a method of linking one or more buffering groups to a candidate immobilized buffer particle, wherein the click chemistry reactive functionality is an azide, and the click chemistry complementary functionality is an alkyne.

In some embodiments, the disclosure relates generally to a method of linking one or more buffering groups to a candidate immobilized buffer particle, wherein the click chemistry reactive functionality or complementary functionality is linked to a polyacrylamide polymer matrix.

In some embodiments, the disclosure relates generally to an apparatus comprising: a flow cell containing one or more immobilized buffer particles and one or more confinement regions, at least one confinement region including one or more electrically charged zones, and at least one immobilized buffer particle having an electrical charge that is the same polarity as the electrical charge of at least one of the one or more charged zones; wherein at least one of the particles is linked to one or more immobilized buffering groups, at least one of the one or more immobilized buffering groups having a known pKa within a predetermined range.

In some embodiments, the disclosure relates generally to an apparatus, further including a pH sensor operationally associated with at least one of the one or more confinement regions for measuring transient pH values of the reagent in such at least one confinement region.

In some embodiments, the disclosure relates generally to an apparatus, wherein the pH sensor includes an ISFET.

In some embodiments, the disclosure relates generally to an apparatus, wherein at least one of the one or more immobilized buffering groups has a pKa within a predetermined range; effective to buffer the aqueous reagent at a predetermined pH value.

In some embodiments, the disclosure relates generally to an apparatus, wherein the at least one or more immobilized buffering groups has a pKa in the range of about 4.5 to about 9.0.

In some embodiments, the disclosure relates generally to an apparatus, wherein the at least one or more immobilized buffering groups has a pKa in the range of about 6.0 to about 8.0.

In some embodiments, the disclosure relates generally to an apparatus, wherein the one or more buffering groups is selected from the group consisting of triethanolamine, N-[tris(hydroxymethyl) methyl]-2-aminoethanesulfonic acid, 3-(N-tris[hydroxymethyl]methylamino)-2-hydroxypropanesulfonic acid, N-(2-hydroxyethyl)piperazine-N-(2-ethanesulfonic acid), N-(2-acetamido)-2-aminoethanesulfonic acid, imidazole, and acetate.

In some embodiments, the disclosure relates generally to an apparatus, wherein the average diameter of the one or more immobilized buffer particles is smaller than the average diameter of the at least one confinement region.

In some embodiments, the disclosure relates generally to an apparatus, wherein the average diameter of the one or more immobilized buffer particles is greater than the average diameter of the at least one confinement region.

In some embodiments, the disclosure relates generally to an apparatus, wherein the at least one confinement region includes, or is associated with, at least one sensor selected from the group consisting of: a sensor for detecting an analyte of interest, or with a sensor for detecting the pH of a solution within the confinement region.

In some embodiments, the disclosure relates generally to an apparatus, wherein the immobilized buffer particle has a size that is larger than at least one diameter of a confinement region of an apparatus for detecting an analyte of interest.

In some embodiments, the disclosure relates generally to an apparatus for measuring pH values, the apparatus comprising: a volume defined by at least one surface having one or more confinement regions, the volume containing a reagent with immobilized buffer particles having an average size and shape such that substantially no immobilized buffer particles can enter any confinement region; and a pH sensor operationally associated with at least one confinement region for measuring transient pH values of the reagent in such at least one confinement region.

In some embodiments, the disclosure relates generally to an apparatus for measuring pH values, wherein said immobilized buffer particles have a buffer capacity and a concentration effective to maintain said reagent in said volume at a substantially constant pH except within the confinement regions, and wherein said reagent in at least one of said confinement regions may have a transient pH different from the substantially constant pH of said volume, such that the transient pH may be measured by said pH sensor.

In some embodiments, the disclosure relates generally to an apparatus for measuring pH values, wherein said immobilized buffer particles include one or more spheroidal polyacrylamide particles having one or more immobilized buffering groups having a preselected pKa.

In some embodiments, the disclosure relates generally to an apparatus for measuring transient pH values, the apparatus comprising: a volume of reagent defined by at least one surface having one or more confinement regions in fluid communication therewith, the reagent containing immobilized buffer particles having an average size and shape such that substantially no immobilized buffer particles can enter any confinement region; and a pH sensor operationally associated with at least one confinement region for measuring transient pH values of the reagent in such at least one confinement region.

In some embodiments, the disclosure relates generally to an apparatus for measuring transient pH values, wherein the sensor is a chemFET.

In some embodiments, the disclosure relates generally to an apparatus for measuring various properties, the apparatus comprising: a chamber having at least one confinement region, said confinement region having one or more charged zones; an immobilized buffer particle present within the apparatus, wherein the immobilized buffer particle has an electrical charge that is the same polarity as the electrical charge contained in the one or more charged zones of the at least one confinement region of the apparatus, and a sensor operationally associated with at least one confinement region for measuring values of various properties of the reagent in such at least one confinement region.

In some embodiments, the disclosure relates generally to an apparatus for measuring various properties, the apparatus comprising: a chamber having at least one confinement region, said confinement region having one or more charged zones; an immobilized buffer particle present within the apparatus, wherein the immobilized buffer particle has an electrical charge that is the same polarity as the electrical charge of a confinement region of an apparatus for detecting an analyte of interest, wherein the charged immobilized buffer particle is inside a chamber of the apparatus that includes confinement regions.

In yet a further embodiment, the disclosure provides an immobilized buffer composition comprising a plurality of immobilized buffer particles suspendable in an aqueous reagent, each immobilized buffer particle having thereon one or more immobilized buffering groups. In various exemplary embodiments, the one or more immobilized buffering groups may each have a known pKa, and therefore may specifically be selected to buffer the aqueous reagent at a predetermined pH value. In one embodiment, the immobilized buffer composition particles are chosen from polyacrylamide particles.

The disclosure also relates to methods of making novel immobilized buffer particles having one or more buffering groups linked to the particles.

The disclosure further relates to systems and apparatuses for controlling pH in bulk reagents that are delivered to reactions confined to local regions, such as arrays of reactions, when transient pH values are being measured in such confinement regions. In at least one embodiment, the disclosure provides systems for measuring transient pH values comprising the following elements: (a) a volume defined by at least one surface having one or more confinement regions, the volume containing a reagent including one or more immobilized buffer particles; and (b) a pH sensor operationally associated with at least one confinement region, configured to measure transient pH values of the reagent in such confinement region. In some embodiments, the sensor is able to measure and detect an analyte of interest other than pH, and on various molecules other than DNA. In some embodiments, at least one of the one or more confinement regions is configured to substantially exclude the one or more immobilized buffer particles. In some embodiments, the one or more immobilized buffer particles have an average diameter that is greater than the average diameter of the one or more confinement regions of the apparatus. In some embodiments, the one or more immobilized buffer particles can have an average diameter that is greater than the diameter of at least one confinement region in any single dimension. In some embodiments, the immobilized buffer particles each have a size and shape such that substantially none (e.g., few to none) of the immobilized buffer particles can enter any confinement region.

The disclosure relates to a number of implementations and applications, some of which are summarized below and throughout the specification.

BRIEF DESCRIPTION OF THE DRAWINGS

The accompanying drawings are included to provide a further understanding of the disclosure, and are incorporated in and constitute a part of this specification. The drawings are not intended to be restrictive of the disclosure as claimed, but rather are provided to illustrate exemplary embodiments of the present teachings and, together with the description, serve to explain certain principles. In the drawings.

DETAILED DESCRIPTION OF EXEMPLARY EMBODIMENTS

Figure 1:
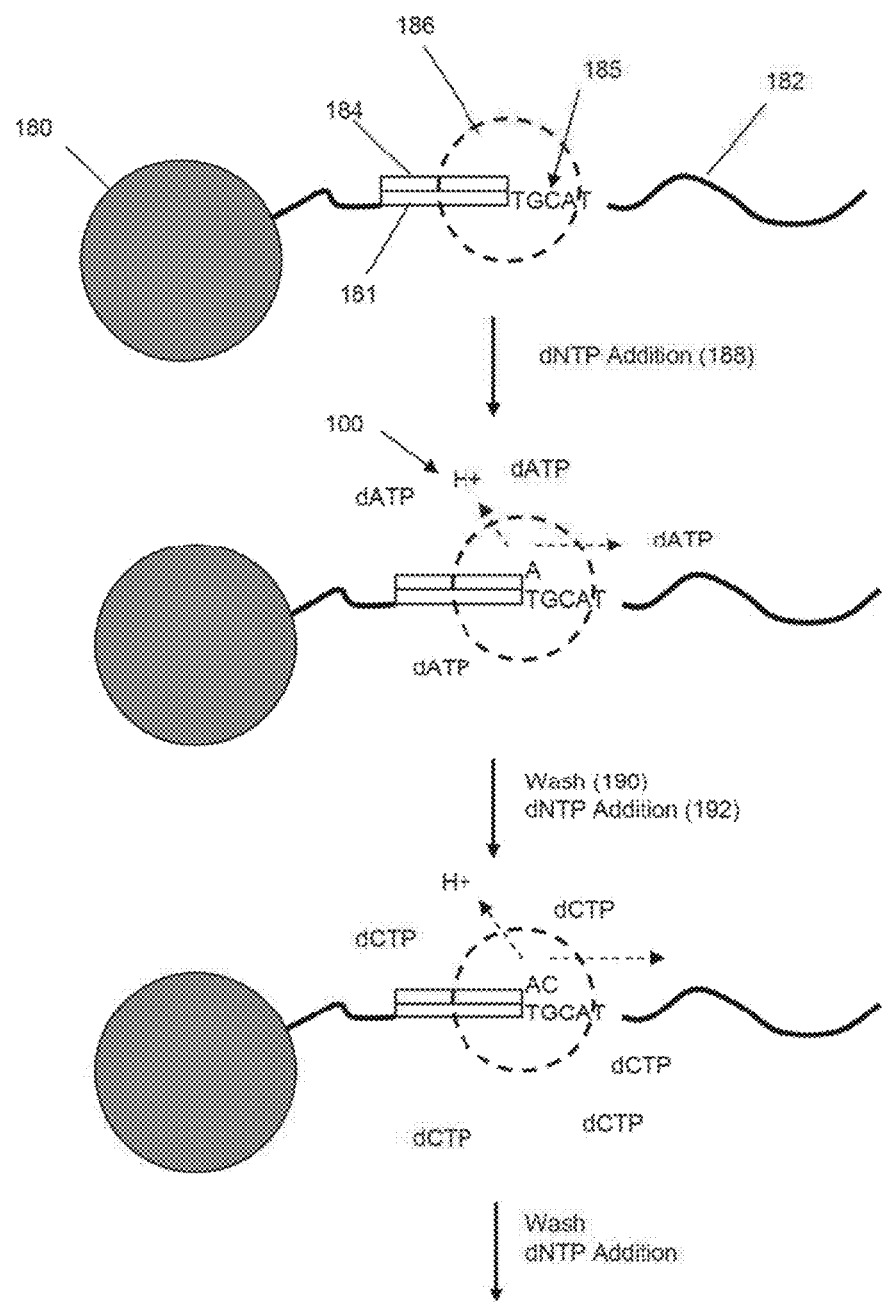
FIG. 1 illustrates steps in a pH-based DNA sequencing method.

While the disclosure is amenable to various modifications and alternative forms, specifics thereof have been shown by way of example in the drawings and will be described in detail. It should be understood, however, that the intention is not to limit the disclosure to the particular embodiments described herein. On the contrary, the intention is to cover all modifications, equivalents, and alternatives falling within the spirit and scope of the disclosure. There is guidance in the art for the application of conventional techniques used in connection with the disclosure, such as the following exemplary references, which are incorporated herein by reference: *Genome Analysis: A Laboratory Manual Series* (Vols. I-IV), *PCR Primer: A Laboratory Manual*, and *Molecular Cloning: A Laboratory Manual* (all from Cold Spring Harbor Laboratory Press), Hermanson, *Bioconjugate Techniques*, Second Edition (Academic Press, 2008); Merkus, *Particle Size Measurements* (Spring, 2009); Rubinstein and Colby, *Polymer Physics* (Oxford University Press, 2003); and the like. There is also guidance in the art for carrying out electrochemical measurements of the disclosure, such as the following exemplary references, which are incorporated herein by reference: Sawyer et al., *Electrochemistry for Chemists*, $2^{nd}$ edition (Wiley Interscience, 1995); Bard and Faulkner, *Electrochemical Methods: Fundamentals and Applications*, $2^{nd}$ edition (Wiley, 2000); and the like.

The disclosure relates to compositions, methods, apparatuses, and systems for measuring transient pH values. At least one exemplary embodiment of the disclosure provides an apparatus for measuring pH values comprising (a) a volume defined by at least one surface having one or more confinement regions, the volume containing a solution or reagent mixed with immobilized buffer particles each having a size and shape such that few to no immobilized buffer particles can enter the one or more confinement regions, and (b) a pH sensor operationally associated with the one or more confinement regions, configured to measure pH values of the solution in the one or more confinement regions. In some embodiments, the pH values measured by the apparatus are transient pH values. The term "transient," as used herein, is intended to describe a state when a process variable is not permanent or is changing over time. By way of example, "transient" will be used throughout the disclosure in connection with the pH of a reaction, which may vary at different points in time during the reaction. As such, the terms "transient," "variable," "variation," and the like, may be used interchangeably herein with respect to pH value.

As one of skill in the art will appreciate, parameters of the systems and apparatuses described herein, such as configurations of the volume, at least one surface, and confinement regions, may vary. In various embodiments, the volume is defined by a chamber, and the at least one surface may be, for example, a wall of the chamber or a surface of a substrate placed in a chamber. The one or more confinement regions may be in a variety of shapes or configurations such as, for example, cavities, microwells, capillaries, tubing, and the like, and may be formed in a surface of a chamber or other substrate in fluid communication with the chamber. In at least one exemplary embodiment, the one or more confinement regions may be separated from an interior of the chamber by a membrane permeable to a solution or reagent, yet impermeable to immobilized buffer particles.

The terms "chamber," "reaction chamber," "confinement region," "cavity," and the like, are used interchangeably throughout this disclosure. These terms are meant to signify areas that hold a particular volume of a mixture, solution, or the like, and are formed within the apparatus and systems described herein. The terms may be used to represent one or several of the volumes within one or more apparatuses or systems. These terms are not meant to be limiting.

In various embodiments, pH variation in one or more confinement regions may optionally be sufficiently separated from a larger chamber of the apparatus, such that diffusion of hydrogen ions in the region of variable pH to a pH sensor occurs faster than diffusion to immobilized buffer particles in the larger chamber. For example, where confinement regions are microwells, the dimensions and aspect ratio (depth:diameter) of microwells may be selected so that the location of the variable pH, such as, for example, reactions on a bead in the microwell, fulfill such a condition.

In some embodiments, the apparatus and the immobilized buffer particles included therein are configured to ensure that the buffering effect of the particles is selectively localized to desired locations or regions within the apparatus. For example, one or more regions or locations of the apparatus (for example, at least one confinement region) can be configured to exclude the immobilized buffer particles, such that the one or more regions remain substantially unbuffered while the other locations of the apparatus remain at relatively constant pH due to the buffering effect of the immobilized buffer particles. In some embodiments, at least one confinement region of the apparatus remains substantially unbuffered and includes a reactive zone wherein ions (e.g., hydrogen or hydroxyl ions) are produced as a byproduct of a chemical reaction occurring within the reactive zone. The confinement region can also be associated with a sensor that is capable of sensing the production of such ions.

In one exemplary embodiment, the sensor can be a pH sensor that is capable of sensing the presence of hydrogen ion byproducts. Hydrogen ions responsible for variable pH in a confinement region should be close enough to be detected by a pH sensor before reacting with buffering groups of the immobilized buffer particles. In other embodiments, the sensor can be a sensor for heat measured before, during, and after the reaction(s) occurring in the apparatus. In other embodiments, the sensor can be a sensor for phosphates or other reactants and molecules within the apparatus. In still other embodiments the sensor is able to detect an analyte of interest and measure levels of said analyte. In other embodiments, the sensor is able to detect and measure levels of various physical and chemical properties of molecules other than DNA. Importantly, as can be understood by one of skill in the art, there are many properties that affect the pH levels of a mixture, solution or reaction. Those listed here are only a few of those that can alter the pH measurements. These properties can be measured in relation to pH levels or independently for various other detection purposes. Regardless, it can be important and necessary to monitor and measure several other properties and analytes in addition to just pH. In at least certain exemplary embodiments, the confinement regions, sensors and immobilized buffer particles are configured to ensure effective buffering of the bulk reagents in the main body of the flow cell, while the amount of interference received by the pH sensor from external elements, such as, for example, buffering agents, within the confinement regions is at a minimum or not present at all.

The use of immobilized buffer particles to selectively target buffering capacity to desired regions of the apparatus provides several advantages, chiefly the ability to buffer the bulk reagent within the flow cell and thus prevent "drift" in pH of the bulk reagent over time, while minimizing buffering within the confinement regions and thus preventing interference with the ability of the sensors to sense transient pH changes occurring at the reactive sizes within the confinement regions.

As such, in various embodiments of the disclosure, it may be advantageous that the size and/or shape of the confinement regions and/or particles may be chosen to optimize the process, such as by minimizing interference received by the pH sensor from external elements, such as, for example, buffering agents. By way of example, the size of the immobilized buffer particles may be chosen to be larger than the diameter of the confinement regions, thereby preventing the particles from entering the confinement regions and causing interference with the pH sensor. In various embodiments, it may further be advantageous that the size of the immobilized buffer particles is chosen so that it is larger than the diameter of the confinement regions, but of a size that the particles can maintain a spatial relation to the confinement regions where the particles are able to properly serve as a buffer in the solution and apparatus/array. In yet further embodiments, it may be advantageous that the size of the immobilized buffer particles is smaller than at least one diameter of the confinement regions, such that the particles can enter the confinement regions without clogging the apparatus and array system.

In further embodiments, the shape and/or configuration of the confinement region and/or particles may optionally be chosen to optimize the process, such as, for example, to reduce interference received by the pH sensor from external elements, including, for example, buffering agents. For example, in an embodiment where the confinement region is a microwell, the microwell may be any shape, such as, for example, cylindrical, conical, angular, tubular, tapered, and the like. The confinement region may also optionally be configured such that it does not have a uniform diameter throughout the region, which may, in various embodiments, prevent the particles from entering or wholly entering the confinement region. For example, a microwell may have at least one diameter at the upper portion of the well that is larger than that of the lower portion of the well. For example, the diameter of the upper portion may be in the range of about 3.1 um or 3.2 um, and the diameter of the lower portion may be in the range of about 2.3 um to 2.5 um. In other exemplary embodiments, the microwell may have an upper diameter of about 1.3 um to 2.0 um and a lower diameter of 0.5 um to 1.0 um. This may, in various embodiments, allow one or more particles to enter the well, but not completely.

In another exemplary embodiment, when a surface or substrate in which confinement regions are present has an electrical charge under operating conditions, immobilized buffer particles may optionally be made with a like polarity so as to minimize access to the confinement regions by the particles. In various exemplary embodiments, the confinement regions formed in the chamber may have an electrical charge or may contain "zones" or portions of the surface of the confinement region that are electrically charged. The charged zones of the confinement regions may have the same polarity as the immobilized buffer particle used in the reaction. The charged zones of the confinement regions may have variable polarity, such as, for example, depending on the material of which the confinement regions is made of or the contents of the confinement regions, or the confinement region may be treated to have an electrical charge. By way of example, the confinement region may be made of a material, such as a metal oxide-based material, creating a negative charge in the confinement region, or, as a further example, the charged zones may have a negative charge when DNA is present in the confinement region.

Additionally, metal nitrides may be useful as a coating that senses pH as well, and it would also impart a negative charge to the surface it coated. Furthermore, it is possible to coat or functionalize a metal oxide surface with a wide variety of chemical groups that are bound to a linker reactive with metal oxide. There are also a variety of negatively charged groups that can be linked to the buffer particles and these same groups may be linked to the DNA in the form of beads, for example, as well. By way of non-limiting example only, 2-Acrylamido-2-methyl-1-propanesulfonic acid may be used to impart a negative charge, and (3-Acrylamidopropyl)trimethylammonium chloride may be used to impart a positive charge on gel particles.

In a further exemplary embodiment, the immobilized buffering particles thus may optionally be chosen from materials that have a polarity that is the same as that of the charged zone of the confinement region. For example, when the confinement region has a negative charge, the particles may also have a negative charge, or may be treated to have a negative charge. By way of example only, when the immobilized buffer particles are comprised of polyacrylamide, they may be treated to have a negative charge. It is well within the ability of those skilled in the art to select particles having an appropriate polarity or treat particles to have an appropriate polarity for use in the methods described herein. By way of example, methods of treating particles to impart a particular polarity are well-known, and may include but are not limited to techniques such as those described in the following reference, which is hereby incorporated by reference: Ziberstein et al., *Anal. Chem.*, 80: 5031-5035 (2008); and the like.

Thus, it is an advantage of the present disclosure that the size, shape, and/or polarity of the immobilized buffer particles and confinement regions of the systems and apparatuses may be chosen to optimize the process and provide a desired result. This may allow, for example, more flexibility in selecting materials to use for the confinement regions as well as selecting buffering groups that affect the charge of the immobilized buffer particle. For example, a smaller-sized particle can be used in the system and because of the like polarity, it will not enter the well, or, if it does enter the well it will not interfere with the pH sensor and/or will not settle in the well or throughout the system, even after an extended period of reaction time. Therefore, there will be less or even no clogging of the system from the use of gel- or polymer-based particles, as is common in existing models where larger particles are used as buffering agents.

As an example, as described herein, one of skill in the art may choose a size and/or shape of the buffering particles and/or confinement regions such that the buffering particles are smaller in diameter than at least one diameter of the confinement region. However, in an embodiment where the buffering particles are electrically charged particles with a charge that is the same polarity as the charge of the confinement regions, the immobilized buffer particle can enter the confinement region without causing clogging or interference with the pH sensor in the apparatus and array system. If, for example, a small, negatively charged immobilized buffer particle is used throughout a system that has relatively larger confinement regions with negatively charged zones, the particles will run though the apparatus without interfering with the pH sensor of the hydrogen ion signal to noise ratio.

In further exemplary embodiments, the immobilized buffer particles may be very long and/or large particles, including a single long chain of polymers. These "macro-molecular" buffering particles have a very high molecular weight and are able to function in the same or similar way as the smaller particles. The "macro-molecular" buffering concept is, at least in part, based upon controlling a chemical potential such as buffering through diffusion for temporally dependent signals. In the specific ion sequencing case, if a buffering molecule cannot move away from the polymerase/bead proton source during the measurement of the polymerase proton pulse then the total proton signal may be maintained, and in some instances stretched out, in spite of an increased overall buffering capacity. The species responsible for modulating the chemical event are expected to not move or diffuse significantly over the measurement period, while allowing for a different equilibrium condition to occur over longer times. Since the actual incorporation signal is a modest time fraction of each nucleotide flow, the effects of buffering during this period can be different from those reached over the entire flow period.

By way of non-limiting example, diffusion rates may be important parameters in some embodiments to reduce proton signal loss from wells with beads. The large scale and long range buffering is designed and intended to occur over time, while reducing the buffered proton movement out of wells over the shorter measurement period by slowing down the buffer's diffusion rate. It is possible that with the replacement of NaOH for bead find with high MW buffers, these measurements can be realized. In this exemplary embodiment, certain advantages can be realized, for example, diffusion of high molecular weight species with a high pKa, such as, for example, pKa2>pH 10, into empty wells will be much faster and produce a greater transient signal than wells with beads.

By way of comparison and as a further non-limiting example, the particle buffering concept may be able to control the local chemistry by exclusion or inclusion based on the spatial dimensions of the particle. This is a static or equilibrium mechanism and is based upon a different type of molecular property, than for example the macro-molecule buffer. While these two mechanisms are related since diffusion rates decrease as molecular length scales grow, it is important to note that diffusion can also be changed in ways such as a drag force from an ion atmosphere that is not strictly due to particle size. While the examples set forth herein describe large polymers with low diffusion rates, it is possible that other exemplary embodiments include other slow diffusing species, such as, for example, 50-200 nm particles (<<well & bead sized), which can easily enter and exit wells.

By way of a further non-limiting example, it is possible to use several different high molecular weight compounds, such as those listed here. For example, 5 & 20 kDa PEGs with a single tris moiety may be used. These PEGs molecules are not as large as is possible and demonstrate appreciable diffusion rates while having the ability reduce the pgmproton signal. In another example, vinyl phosphonate incorporated at low ratio into linear polyacrylamide (MW ranging from ~200,000 to >1,000,000 and input phosphonate/LPA molar ratios from ⅒ to ⅕₀₀₀) may be used. Here, the phosphonate can be incorporated into the high MW LPA by P31 NMR (ratio unknown). In general, these compounds exhibit qualities such that they stick well to Ta2O5 surfaces and can competitively block a dye labeled phosphate probe. In still another example, vinyl morpholino, also incorporated in LPA, can be used. The vinyl morpholino monomer is able to inhibit LPA polymerization.

In further exemplary embodiments, an apparatus according to the disclosure may be a component of a larger apparatus for carrying out multi-step reactions that include monitoring of one or more transient pH signals. Such multi-step reactions may be cyclic, such as in DNA sequencing reactions, where repeated cycles of one or more steps are carried out, or they may be non-cyclic, such as in multi-component labeling reactions, as for example, in a sandwich assay using enzymatic labels. Multi-step reactions may also result from the presence of a biological material, such as living cells or tissue sample, where responses, e.g., the presence or absence of metabolites, are detected in response to a series of reagent exposures, which may be drug candidate molecules, or the like. In some cases, electronic pH sensors may be integrated into a sensor array suitable for sensing individual reactions taking place on or adjacent to a surface of the array. For example, an array of reaction confinement regions may be integrated with such a sensor array. An array of reaction confinement regions may, for example, take the form of a microwell array made by conventional micro- or nanofabrication techniques, for example, as described in Rothberg et al., U.S. Patent Publication US2009/0127589 and Rothberg et al., U.K. Patent Application No. GB24611127.

In one exemplary embodiment, each microwell or confinement region in such an array has at least one sensor that is in a sensing relationship so that pH changes due to a reaction in the microwell or confinement region can be detected and/or measured. The structure and/or design of sensors for use with such apparatus may vary, as exemplified by the following references, which are incorporated herein by reference: Rothbert et al., U.S. Patent Publication No. US2009/0127589; Rothberg et al., U.K. Patent Application No. GB24611127; Barbaro et al., U.S. Pat. No. 7,535,232; Sawada et al., U.S. Pat. No. 7,049,645; Kamahori et al., U.S. Patent Publication No. 2007/0059741; Miyahara et al., U.S. Patent Publication No. 2008/0286767 and 2008/0286762; O'uchi, U.S. Patent Publication No. 2006/0147983; Osaka et al., U.S. Patent Publication No. 2007/0207471; Esfandyarpour et al., U.S. Patent Publication No. 2008/0166727; and the like. In at least one embodiment, sensors of an array comprise at least one chemically-sensitive field effect transistor that is configured to generate at least one output signal related to pH in proximity thereof. Such properties may include a concentration (or a change in concentration) of a reactant or product, or a value of a physical property (or a change in such value), such as temperature.

In further various embodiments, the sensor used in the apparatus can measure additional physical and chemical properties beyond that of pH levels. For example, the sensors used in the apparatus can measure heat and temperature of a reaction and solution running through the apparatus, as well as different chemical levels, such as, for example, phosphate and other analyte levels within the reaction solutions.

The disclosure further relates to systems for maintaining bulk reagents of a fluidly connected system at a substantially constant pH, while permitting local transient variations in pH to arise and be measured. More specifically, the disclosure relates to compositions comprising a novel solid state buffering agent, including methods of making and using a novel solid state buffering agent and apparatuses for the same. A novel solid state buffering agent is also disclosed.

In one embodiment of the disclosure, a solid state buffering agent is a composition of immobilized buffer particles for buffering the pH of one or more reagents at a predetermined value. As used herein, "bulk reagent" refers to a reagent in a fluidics system occupying volume or space therein accessible to immobilized buffer particles. The immobilized buffer particles may have a wide variety of physical properties (e.g., density, polarity), chemical compositions, sizes, shapes, and buffering concentrations and capacities, depending on particular applications, some of which are described herein. In one aspect, the density and size of immobilized buffer particles are selected so that they remain suspended in reagents being buffered without stirring. In another aspect, immobilized buffer particles have a defined size distribution such that few to no particles can enter or access confinement regions within a larger chamber, so that local transient pH values can occur in such confinement regions, without interference from the buffering effect of the immobilized buffer particles. In a further exemplary embodiment, substantially no immobilized buffer particles that can enter or access the confinement region. In further exemplary embodiments, the amount of immobilized buffer particles that can enter or access the confinement region can be defined as not greater than about 10%. For example, in various embodiments, no more than about 5%, about 2%, or about 1% of the confinement regions are occupied by one or more immobilized buffer particles.

Immobilized buffer particles may be porous having buffering groups throughout their interiors. Buffering groups may include any moieties having a determinable pKa that may be covalently linked to or integrated in an immobilized buffer particle. Examples of buffering groups and their structures that may be linked or integrated as moieties in the immobilized buffer particles include, but are not limited to: triethanolamine:

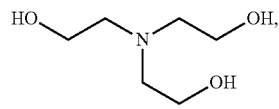

N-[tris(hydroxymethyl)methyl]-2-aminoethanesulfonic acid:

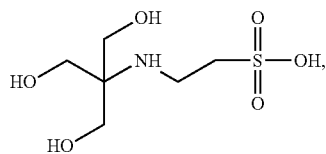 [SMILES: O=S(=O)(O)CCNC(CO)(CO)CO]

3-(N-tris[hydroxymethyl]methylamino)-2-hydroxypropanesulfonic acid:

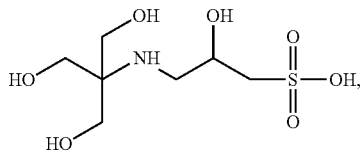 [SMILES: O=S(=O)(O)CC(O)CNC(CO)(CO)CO]

N-(2-hydroxyethyl)piperazine-N-(2-ethanesulfonic acid):

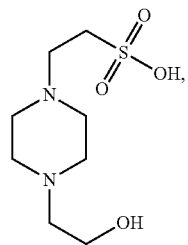 [SMILES: O=S(=O)(O)CCN1CCN(CCO)CC1]

N-(2-acetamido)-2-aminoethanesulfonic acid:

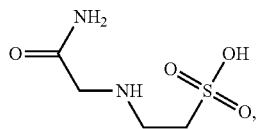

imidazole:

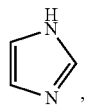

and
acetate:

Buffering groups may also be chosen according to a predetermined pKa of the buffering group. For example, the predetermined pKa values of solution phase buffering groups may include a range of from about 4.5 to about 9.0, such as, for example, about 6.0 to about 8.0. By way of example only, the predetermined pKa values of the buffering groups may be chosen from about 4.76, about 6.8, about 6.9, about 7.5, about 7.6 and about 7.8. As will be known by one of skill in the art, the pKa of the immobilized adduct can differ slightly based on where the buffering moiety is linked to the polymer backbone. In one exemplary embodiment, immobilized buffer particles are chosen from polyacrylamide particles. The polyacrylamide particles may be made by any method known, such as, for example, by using precursors that include acrylamide acids and/or bases (Immobiline™ compounds). See, e.g., Chiari et al., *Electrophoresis*, 13: 187-191 (1992); Righetti, *Immobilized pH Gradients: Theory and Methodology* (Elsevier, 1990); U.S. Pat. No. 4,971,670, which are incorporated herein by reference. In various embodiments, when desired, size, density, and pH buffering characteristics may be controlled by using well-known techniques for making polyacrylamide particles. In one exemplary embodiment, immobilized buffer particles are compositions of spheroidal particles having a diameter in the range of from about 0.5 µm to about 100 µm. In further embodiments, immobilized buffer particles are compositions of spheroidal particles having a diameter in the range of from about 100 nm to about 500 nm. In yet further embodiments, the immobilized buffer particles can have a diameter in the ranges of from about 10 µm to about 15 µm, or about 12 µm to about 18 µm. In yet further embodiments, the size distribution of particles in such compositions has a coefficient of variation of up to about 50%, such as up to about 25%. In various embodiments, similar to that described above, the immobilized buffer particles may be electrically charged particles wherein the particle has a charge that is the same polarity as the charge of the confinement region and opposite the charge of other cells or molecules contained in or passing through the confinement regions. For example, the immobilized buffer particle may carry a negative charge which is the same polarity as that of the charge of a zone in a confinement region, causing the immobilized buffer particle to repel the confinement region reducing interference with the pH sensor and promoting full interaction and reactions between the other target molecules in the confinement region carrying a positive charge. As previously described, this may be advantageous such that it may allow the flexibility of being able to use a wide range of different sized particles with the apparatus. For example, a smaller particle that carries a charge that is the same polarity as that of the charge of the confinement region may be used through the apparatus without the particle settling within the confinement region otherwise leading to possible clogging of the apparatus. Additionally, the like charged immobilized buffer particles will not interfere with the sensors in the apparatus.

Compositions

As mentioned above, immobilized buffer particles may be made of a variety of materials, including conventional particles and beads with reactive groups on their surfaces for attaching buffering groups. See, e.g., Bangs Laboratories (Fishers, Ind.). Immobilized buffer particles comprising gels or polymer networks are particularly useful in that buffering groups may be incorporated throughout a volume of the particles thereby permitting greater buffer concentration for the same mass of particles. As used herein, the term "incorporated" and variations thereof, is intended to mean linked to a structure, such as by covalent linkage, for example, copolymerization, non-covalent bonds, such as streptavidin-biotin, and hydrogen bonding of DNA-like molecules. As used herein, the terms "polymer particles," "polymer network," "porous microparticle," and variations thereof, may be used interchangeably and are intended to mean a structure comprising covalently connected subunits, such as monomers, crosslinkers, and the like, in which all such subunits are connected to every other subunit by many paths through the polymer phase, and wherein there are enough polymer chains bonded together (either physically or chemically) such that at least one large molecule is coextensive with the polymer phase, i.e. the structure is above its gel point. In various embodiments, the polymer particles may have a volume in the range of from about 65 aL to about 15 pL, or from about 1 fL to about 1 pL.

The polymer networks useful according to the disclosure include, but are not limited to, those set forth in U.S. Patent Application Publication No. 2010/0304982 A2, which is incorporated herein by reference. Those skilled in the art will appreciate that the parameters for making polymer networks can be varied, depending on, for example, the desired properties. Such parameters include, but are not limited to, the following: (i) the hydrophilicity of polymers of the network, (ii) whether the polymers are capable of having a pore and/or network structure (e.g., average pore diameter, tortuosity, and the like) that permits interior access to solvents or reagents being used, (iii) whether the polymers are physically and chemically stable under operating conditions where biomolecules, such as enzymes, are functional, and (iv) whether the polymers are amenable to incorporation of buffering groups. There is guidance in the art for selecting polymers and polymerization methodologies to produce polymer networks meeting such performance criteria, such as the following exemplary references, which are incorporated by reference: Saltzman and Langer, *J. Biophys.*, 55:163 (1989); Ghosh et al., U.S. Pat. No. 5,478,893; Mirzabehov, U.S. Pat. No. 6,656,725; Johnson et al., U.S. Pat. No. 6,372,813; Tang and Xiao, *Biosensors and Bioelectronics*, 24: 181701824 (2009) Boles et al., U.S. Pat. Nos. 5,932,711 and 6,180,770; Xiao et al., *Electrophoresis*, 28: 1903-1912 (2007); Holmes et al., *Electrophoresis*, 12: 253-263 (1991); Shapero et al., *Genome Research* 11: 1926-1934 (2001); Righetti et al., *J. Biochem. Biophys. Methods*, 4: 347-363 (1981); Mitra et al., *Nucleic Acids Research*, 27: e34 (1999); Rehman et al., *Nucleic Acids Research*, 27: 649-655 (1999); Smith, U.S. Pat. No. 4,485,224; Chiari et al., U.S. Pat. No. 5,785,832; Richwood and Hames, Editors, *Gel Electrophoresis* (CVH, Deerfield Beach, 1985); Mitra et al., *Anal. Biochem.*, 320: 55-65 (2003); Kenny et al., *Biotechniques*, 25: 516 (1998); Elaissari, Editor, *Colloidal Polymers: Synthesis and Characterization* (Marcel Dekker, Inc., New York, 2003); and the like.

In various exemplary embodiments, polymer networks may comprise one or more polymers chosen from agarose, polyoxybutylene, diethylacrylamide, polyoxyethylene, polyacrylamide, polyoxypropylene, N,N-polydimethylacrylamide, poly(N-isopropylacrylamide), polyvinylpyrrolidone, poly-N-hydroxyacrylamide, vinyl-based polymers such as polyvinylphosphonate, and the like. As described more fully below, such polymers may be formed into polymer networks using any method known to those of skill in the art, such as, for example, cross-linking methods, methods for producing desired shapes, and the like.

Accordingly, in at least one embodiment of the disclosure, the polyacrylamide particle composition may comprise a population of polyacrylamide particles with an average particle size of less than about 15 μm, such as, for example less than about 10 μm, or less than about 5 μm. By way of example only, the particles may have an average particle size of about 1.5 μm. The polyarcrylamide particles may have a coefficient of variation of less than about 20%, for example less than about 15%. In at least one embodiment, the polyacrylamide particles may have a weight:volume percentage of about 25% or less. In another embodiment, the polyacrylamide particles may be spheroidal and have an average diameter of less than about 15 μm, with a coefficient of variation of less than about 20%.

In various exemplary embodiments, the methods of making polymer particles comprise the steps of making polymer networks that incorporate either bromoacetyl groups or alternative thiol groups, reacting either a thiolderivatized buffering group or a bromoacetyl-derivatized buffering group respectively, as taught by Ghosh et al., U.S. Pat. No. 5,478,893, which is incorporated herein by reference. Synthesizing bromoacetyl-derivatized and thiol-derivatized molecules is further disclosed by Gryaznov, U.S. Pat. No. 5,830,658, which is incorporated herein by reference. In one exemplary embodiment according to the disclosure, polyacrylamide particles may be chosen that may be size-selected either before or after bromoacetyl- and thiol-derivatized components are reacted.

In various exemplary embodiments, generic incorporation of a functional handle allows the attachment of buffering moieties via a multitude of conjugation chemistries. A functional handle, as can be understood by one of skill in the art of synthetic chemistry, is a functional group that allows selective reactivity of it in reference to other functionalities present in the molecule or polymer. Thus, for example, hydroxyethyl groups in polyhydroxyethyl methacrylamide or polyhydroxyethyl acrylamide can be converted into amines by reaction of an activated hydroxyl group (e.g. mesyl, forsyl, tosyl) with sodium azide, followed by reduction with phosphines. The amines can react with activated esters to form amides.

In one exemplary embodiment, a vinyl-based polymer such as polyvinylphosphonate may be used as the buffering group that is copolymerized with divinylbenzene as a cross-linker, and vinyl acetate with post polymerization hydrolysis to yield an alcohol (to some extent, as 100% deactylation is almost never achieved). The resulting alcohol can also be used as a functional handle for post-polymerization attachment of buffering moieties.

In another embodiment, polymer particles can be made by preparing a polymer network that incorporates a click chemistry functionality, so that rapid and specific bonds are formed and an immobilized buffer particle results. Click chemistry functionalities and reactions are well-known and are disclosed in the following references, which are incorporated herein by reference: Lahann, editor, *Click Chemistry for Biotechnology and Material Science* (Wiley, 2009); Kolb et al., *Angew. Chem. Int. Ed.*, 40: 2004-2021 (2001); Binder et al., *Macromolecular Rapid Comm.*, 28: 15-54 (2007); Sharpless et al., U.S. Pat. No. 7,375,234; Carell et al., U.S. Patent Publication No. 2009/0215635; and the like. Reagents containing click chemistry reactive functionalities and complementary functionalities are commercially available from Glen Research (Sterling, Va.); Sigma Aldrich (St. Louis, Mo.), baseclock GmbH (Tutzing, Germany); and like companies. In one exemplary embodiment, the click chemistry reactive functionality is an azide, and the click chemistry complementary functionality is an alkyne. In another exemplary embodiment, a reaction between such functionalities is catalyzed by copper(I). In yet a further exemplary embodiment, a click chemistry reactive functionality or complementary functionality is incorporated into a polyacrylamide polymer matrix.

In various exemplary embodiments, polymer networks comprising polyacrylamide gels may be used. Polyacrylamide gels can be formed by any method known in the art, such as by copolymerization of acrylamide and bisacrylamide ("bis," N,N-methylene-bisacrylamide). The reaction is a vinyl addition polymerization initiated by a free radical-generating system. Polymerization is initiated by ammonium persulfate and TEMED (tetramethylethylenediamine). TEMED accelerates the rate of formation of free radicals from persulfate, and these in turn catalyze polymerization. The persulfate free radicals convert acrylamide monomers to free radicals which react with inactivated monomers to begin the polymerization chain reaction. The elongating polymer chains are randomly crosslinked by bis, resulting in a gel with a characteristic porosity which depends on the polymerization conditions and monomer concentrations. Riboflavin (or riboflavin-5-phosphate) may also be used as a source of free radicals, often in combination with TEMED and ammonium persulfate. In the presence of light and oxygen, riboflavin is converted to its leuco form, which is active in initiating polymerization, which is usually referred to as photochemical polymerization.

In a standard nomenclature for forming polyacrylamide gels, T represents the total percentage concentration (w/v, in mg/mL) of monomer (acrylamide plus crosslinker) in the gel. The term C refers to the percentage of the total monomer represented by the crosslinker. For example, an 8%, 19:1 (acrylamide/bisacrylamide) gel would have a T value of 8% and a C value of 5%.

In various exemplary embodiments, the polymer networks may comprise polyacrylamide gels with total monomer percentages in the range of from about 3% to about 20%, such as in the range of from about 5% to about 10%. In various exemplary embodiments, the crosslinker percentage of monomers may be in the range of from about 5% to about 10%. In additional exemplary embodiments, polymer networks may comprise about 10% total acrylamide, of which about 10% may be bisacrylamide.

Alternatively, in a further exemplary embodiment, immobilized buffer particles can be made by the method of precipitation polymerization comprising the steps of performing a polymerization in a homogenous solution at a temperature above the lower critical solution temperature (LCST), the temperature above which polymers, for example, precipitate out of solution; maintaining an appropriate formulation of monomers and surfactants; and selecting a size and composition of a fully swollen particle. In one aspect, this method allows the generation of such particles as core-shell particles where the core, for example, has a buffering group which may have an overall positive charge and has a shell of a highly negatively charged surface and/or DNA loaded beads. See, e.g., *Macromolecules*, 33, 4354-4360 (2000).

Methods of Making Immobilized Buffering Polymer Particles

Immobilized buffer particles as described herein may be made by a variety of methods. In one aspect, such method include steps of (i) forming a reaction mixture whose polymerization may be controlled by physical conditions, such as, for example, the application of heat or the addition of a catalyst; (ii) performing a polymerization reaction to produce polymer networks or candidate immobilized buffer particles depending on reactants and conditions employed, and (iii) optionally, selecting candidate polymer networks or candidate immobilized buffer particles in a predetermined size range. Immobilized buffer particles may be made by first making polymer networks followed by attachment of buffering groups, or they may be made by co-polymerization of buffering components along with monomers and crosslinkers. In addition to the chemical processes that determine the composition of polymer networks and immobilized buffer particles, physical process are employed to create such networks and particles with desired shapes and size distributions. Such physical processes include, but are not limited to, flow focusing using microfluidics devices, e.g., Nisisako et al., *KabChip*, 8: 287-293 (2008); Kumaresan et al., *Anal. Chem.*, 80: 3522-3529 (2008); pneumatic disruption of a sheath-sample flow stream, e.g., Lin et al., *Biomed Microdevices*, 9: 833-843 (2007); sieving, molding, e.g., Rolland et al., *J. Am. Chem. Soc.*, 127: 10096-10100 (2005); sonication; controlled shearing; and membrane emulsion. Further exemplary references, incorporated herein by reference, include the following: Mak et al. *Adv. Funct. Mater.* 2008 18: 2930-2937; Morimoto et al. *MEMS*2008 Tucson, Az. USA Jan. 13-17, 2008 Poster Abstract 304-307; Lee et al. *Adv. Mater.* 2008 20: 3498-3503; Martin-Banderas et al. *Small*, 2005 1(7): 688-92; and published PCT application WO03/078659.

As used herein, the term "binding pair" and its variants refers to two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions. The two members of a binding pair are referred to herein as the "first member" and the "second member" respectively.

The following may be mentioned as non-limiting examples of molecules that can function as a member of a specific binding pair, without this being understood as any restriction: thyroxin-binding globulin, steroid-binding proteins, antibodies, antigens, haptens, enzymes, lectins, nucleic acids, repressors, oligonucleotides, polynucleotides, protein A, protein G, avidin, streptavidin, biotin, complement component C1q, nucleic acid-binding proteins, receptors, carbohydrates, complementary nucleic acid sequences, and the like. Examples of specific binding pairs include without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; and an oligonucleotide or polynucleotide and its corresponding complement. In one exemplary embodiment of the disclosure, polymer networks may be made by a method of polymerization of acrylamide spray droplets generated by single or multiple nozzles located on an oscillating membrane, such as, for example, in a commercially available system from The Technology Partnership (www.ttp.com), which sprays droplets from single or multiple nozzles located on a stainless steel membrane by piezo electronically actuating the membrane and allowing it to oscillate at its natural resonance frequency. This yields monodispersed droplets in a gaseous atmosphere (such as Argon) at rates of tens of thousands to millions of droplets per second. These droplets are then streamed past a strong UV light source for photoinitiated polymerization. In a further exemplary embodiment, the immobilized buffer particles may be made by a method of polymerization with molding. This approach involves the molding of a paste which disperses the acrylamide, bisacrylamide, and acryldite-labeled oligonucleotides in a sacrificial "porogen" followed by, but not limited to, photoinitiated radical polymerization of the acrylamide monomers with subsequent removal of the porogen by dissolution and repeated washing. The molding technology is available through Liquidia Technologies (Research Triangle Park, N.C.) and disclosed in DeSimone et al., PCT Publication No. WO 2007/024323, and like references. Such approaches are particularly useful for producing non-spheroidal microparticles in defined shapes, such as tetrahedral shapes, hemispherical shapes, barrel shapes, open capsular shapes, toroidal shapes, tube shapes, and the like, which have greater surface areas than spheroidal shaped particles with the same solid volume. In still another embodiment, such polyacrylamide gel is made using acryldite buffering compounds (such as immobilines) so that the resulting non-spheroidal microparticles have covalently attached buffering groups. Alternatively, buffering groups may be attached by using linking groups and chemistries known in the art, such as described above.

In yet a further exemplary embodiment, the immobilized buffer particles may be made by a method of polymerization of emulsified acrylamide, which involves: (a) control of particle size distribution during polymerization, and (b) a controllable polymerization method. Control of size distribution requires both the minimization of polydispersity due to the emulsification process, as well as minimization of instability of the emulsion leading to coalescence of individual drops prior to polymerization. Highly monodisperse emulsions may be achieved through microsieve emulsification techniques, such as, for example, those provided commercially by Nanomi B. V. (The Netherlands), and those disclosed in the following exemplary references, which are incorporated herein by reference: Wissink et al., PCT Publication No. WO2005/115599; Nakajima et al., U.S. Pat. No. 6,155,710; Qiu et al., U.S. Pat. No. 7,307,104; Gijsbertsen-Abrahase, "Membrane emulsification: process principles,": (Ph.D. Thesis, WageningenUniversiteit, 2003); Geerken, "Emulsification with micro-engineered devices": Ph.D. Thesis, University of Twente, ISBN: 90-365-2432-6, 1974; Yuan, et al., "Manufacture of controlled emulsions and particulates using membrane emulsification", Desalination, 224, 2008; Geerken, et al., "interfacial aspects of water drop formation at micro-engineered orifices," *Journal of Colloid and Interface Science*, 312, 2007; Sotoyama, et al., "Membrane emulsification using membranes of regular pore spacing: Droplet size and uniformity in the presence of surface shear," *Journal of Membrane Science*, 323, 2008; Abrahamse, et al., "Analysis of droplet formation and interactions during cross-flow membrane emulsification," *Journal of Membrane Science*, 204, 2002; Katoh, et al., "Preparation of food emulsions using a membrane emulsification system," *Journal of Membrane Science*, 113, 1996; Charcosset, et al., "The membrane emulsification process—A review," *Journal of Chemical Technology and Biotechnology*, 79, 209-219, 2004; and the like.

In one exemplary embodiment, membrane-based emulsification may be used to produce particles. For example, a discontinuous phase (such as an aqueous solution of monomers and other components) is extruded through a plate with multiple through-holes, where the other side of the plate is constantly washed with a stream of continuous phase (such as an oil formulation with surfactant), such that the droplets that break off from the individual orifices are carried away by a stream of continuous phase. The droplet stream is then passed through a heat section of tubing which will initiate the polymerization, and is finally collected in bulk for extraction of the polymer particles.

Alternative procedures for buffering polymer particles may be used in addition to those previously disclosed above, such as for example, extensive dialysis using dialysis membranes in the process of passive diffusion and Tangential Flow filtration, which is an active exchange of wash buffer by filtration and uses a hollow fiber bundle with a size cut-off that is appropriate to retain the particles during the cleaning.

Measuring Size Distributions of Buffering Polymer Particles

In one aspect, size distributions of bulk manufactured polymer networks and/or immobilized buffer particles can be controlled so that their coefficients of variation are as small as possible. For such control, it is helpful to be able to conveniently measure the sizes of a sample of candidate particles to determine whether their populations have appropriate coefficients of variation. Many techniques are available for making such measurements, including, for example, laser diffraction, flow cytometry, coulter counting, image analysis, acoustical spectroscopy, and the like. Instruments for laser diffraction are commercially available from, for example, Malvern Instruments (Malvern, United Kingdom); instruments for flow analysis are commercially available from, for example, Becton Dickinson (San Jose, Calif.); image analysis systems and software are widely available commercially from, for example, Becton Dickinson, BioImaging Systems (Rockville, Md.), and the like. The foregoing techniques for characterizing particles are disclosed in Dukhin and Goetz, *Ultrasound for Characterizing Colloids* (Elsevier Science, 2002); Elaissari, editor, *Colloidal Polymers; Synthesis and Characterization* (Marcel Dekker, Inc., New York, 2003); Shapiro, *Practical Flow Cytometry*, $4^{th}$ edition (Wiley-Liss, 2003); and like references. In the case of polymer networks comprising polyacrylamide, fluorescent monomers are available that may be added to gel reaction mixtures for incorporation into the polymer networks to aid in their tracking and sizing, such as is described in U.S. Pat. No. 5,043,406.

Exemplary Manufacturing Methods

The following implementations can serve as exemplary embodiments of manufacturing methods.

Implementation 1. In this implementation the solid state buffer was a submicron sized hydrogel consisting of a 15% w/v random copolymer of acrylamide (A) (46⅔% of total solids w/w), N-(3-morpholinopropyl)-acrylamide (M) (46⅔% of total solids w/w) and N-methylene bisacrylamide (BA) (6⅔% of total solids w/w). A solution of the monomers in water was added to an oil/surfactant mix (7% w/v Abil WE09, 70% v/v Tegesoft DEC & 23% v/v light mineral oil). The heterophasic mixture was subjected to ultrasonic agitation (horn sonicator at 50% max amplitude for 30 second repeated once). The resulting sub-micron emulsion was mixed with equal volume oil/surfactant mix that shortly before had been saturated with AIBN. The mixture was placed in a force air oven at 90 degrees Celsius for 4 hours under constant rotation. The polymerized nanospheres were recovered from the oil mixture and washed with appropriate surfactant solutions and finally activated by titration to an appropriate constant pH with sodium hydroxide solution (for example, about 7.8).

As can be understood by one of skill in the art, pH is a measure of the acidity or basicity of an aqueous solution. Pure (neutral) water has a pH around 7 at 25° C. (77° F.); this value varies with temperature. When an acid is dissolved in water, the pH will be less than 7 (if at 25° C. (77° F.)). When a base, or alkali, is dissolved in water, the pH will be greater than 7 (if at 25° C. (77° F.)). A solution of a strong acid, such as hydrochloric acid, at concentration 1 mol/L has a pH of 0. A solution of a strong alkali, such as sodium hydroxide, at concentration 1 mol/L, has a pH of 14. Thus, measured pH values will lie mostly in the range 0 to 14. Since pH is a logarithmic scale, a difference of one pH unit is equivalent to a tenfold difference in hydrogen ion concentration. Therefore, when properly adjusted, the pH can be set to reduce the selectivity toward functional groups with the same polarity as a column, or enhance it for oppositely charged functional groups. Similarly, the choice of pH affects the polarity of solutes. Accordingly, one of skill in the art would understand to adjust the pH of the solution being used in the apparatus as disclosed herein according to the desired level of pH being measured for any particular reaction. One of skill in the art would also understand how to use acid-base chemistry procedures well-known in the art to adjust the pH levels accordingly.

Implementation 2: The solutions used in this implementation include SNOIL comprising 73% v/v TEGOSOFT DEC, 20% v/v Mineral Oil, and 7% w/v ABIL WE09; Initiator SNOIL comprising 2% w/v AlBN (A4) mixed into SNOIL under argon via 5 minutes of orbital shaking at speed 6, wherein the saturated solution was allowed to settle for 20 minutes or more before use; and a Polymerization solution comprising 1.) 272.7 mg methylenebisacrylamide (Sigma M7279), 2.) 2.430 g Buffering Acrylamide (N-(3-morpholin-4-yl Propyl) acrylamide), 3.) 13 ml 18 MOhm H2O, and 4.) 9.4 ml 50% wt solution negative acrylamide (Sigma 655821), in this order.

In the polymerization reaction, the SNOIL and the Initiator SNOIL were prepared. Then, using a 50 ml Falcon tube, the Polymerization Solution reagents described above were mixed together in the order listed above. The mixture was capped with argon and vortex and/or rotated until it was completely dissolved. Then, 25 ml of polymerization solution was added to 100 ml of SNOIL in a 250 ml square glass bottle. A stir rod was inserted and the mixture was stirred at 1000 rpm while under argon. A probe sonicator was used at 100% amplitude to sonicate solution for 5 minutes. Then the stir rod was removed with a magnet. 125 ml of Initiator SNOIL was then added to a 250 ml bottle and sealed under argon. The bottled mixture was rotated in 90 C oven for 2 hours. The bottles were removed from the oven and placed in a water bath set at room temperature for five minutes. Ice was added to the water bath and it was allowed to sit for 10 minutes. If necessary, the bottle was placed in 4 C fridge until extraction was performed. During the extraction phase, the polymerized solution was poured out into a six (6) 50 mL Nalgene tubes, which were then spun at 15,000 rpm for 20 minutes. The oil was decanted and 15 mL of butanol was added to the pellet. The pellet was broken by vortexing and physical agitation with a pipetteman. The clumpy solution was then decanted into one 250 mL glass bottle. Another 5 mL of butanol was added to a Nalgene tube, the pellet of which was vortexed. Any remaining clumps were decanted into the same 250 mL glass bottle. The following steps of adding a stir rod through setting the bottles in a room temperature water bath were repeated for two more bottles. (A stir rod was inserted and the mixture was stirred at 1000 rpm while under argon. A probe sonicator was used at 100% amplitude to sonicate solution for 5 minutes. Then the stir rod was removed with a magnet. 125 ml of Initiator SNOIL was then added to a 250 ml bottle and sealed under argon. The bottled mixture was rotated in 90 C oven for 2 hours. The bottles were removed from the oven and placed in a water bath set at room temperature for five minutes.). Then 15 mL of water was added to the 250 mL glass bottles. The same steps noted above were repeated again for the remaining Nalgene tubes. Then the bottle was rotated until the butanol was clear (and a white residue coated the walls), a process which takes approximately 15 minutes. The butanol was decanted by pouring it out. Then 100 mL of 0.1% SDS was added and the 250 mL bottle was shaken at 200 rpm until all the clumps were dissolved.

During the work up, the SDS solution was split into six 50 mL Nalgene tubes and spun down at 15,000 rpm for 30 minutes. The aqueous portion was decanted and the white residue was cleaned from the tubes. Then the tubes were filled with 0.1% SDS and the pellet was resuspended by vortexing. Then the tubes were spun down at 15,000 rpm for 10 minutes. The aqueous portion was decanted and the white residue was cleaned from the tubes. The tubes were filled with 0.1% triton x-100 and the pellet was resuspended by vortexing. Then the tubes were spun down at 15,000 rpm for 10 minutes. The aqueous portion was decanted and the white residue was cleaned from the tubes. The tubes were filled with 15 mL "W2" and the pellet was resuspended by vortexing. The contents of all six tubes were pooled into one, 250 mL plastic container to obtain the concentration and density calculations, three 2 mL microcentrifuge tubes were weighed with 0.1 mg accuracy and the values recorded on the tubes. Then 1 mL of the final solution was spun in weighed 2 mL microcentrifuge tubes for 5 minutes at 21 K rcf. The supernatant was carefully drawn out by slowly screwing up a 1000 uL pipetteman. 1 uL less than the number of displayed after air appeared at the bottom of the pipette tip (X) was recorded. The supernatant was discarded and the tubes were weighed, and the empty weight of the tube (Y) was subtracted out. The following equation was used for the calculations: Concentration(C)=[1000−X]/10=% solids (expect ~10% solids); Density(D)=[Y/(C*10)].

As used in the apparatus of the present disclosure, 1.5 g of immobilized buffer particles per 1 L of W2 were used and the pH of W2 was adjusted to 7.8 with NaOH. The PGM was initialized with an immobilized buffered W2.

To prevent the aggregation of the submicron hydrogel particles and to prevent the settling of solid state buffering particles in wells containing DNA loaded particles a predominately negative charge (at the operating pH) was imparted to the immobilized buffer particles by using 2-acrylamido-2-methyl-1-propane sulfonic acid sodium salt instead of acrylamide. In this implementation, the solid state buffer was a submicron sized hydrogel, which consisted of a 33.5% w/v random copolymer of 2-acrylamido-2-methyl-1-propane sulfonic acid sodium sat (S) (64% of total solids w/w), N-(3-morpholinopropyl)-acrylamide (M) (31% of total solids w/w) and N-methylene bisacrylamide (BA) (5% of total solids w/w). A solution of the monomers in water was added to an oil/surfactant mix (7% w/v Abil WE09, 70% v/v Tegesoft DEC & 23% v/v light mineral oil). The heterophasic mixture was subjected to ultra sonic agitation (horn sonicator at 50% max amplitude for 3+1+1 minutes). The resulting sub-micron emulsion was mixed with equal volume oil/surfactant mix that shortly before had been saturated with AlBN. The mixture was placed in a force air oven at 90 degrees Celsius for 2 hours under constant rotation. The polymerized nanospheres were recovered from the oil mixture and washed with appropriate surfactant solutions and finally activated by titration to an appropriate constant pH with sodium hydroxide solution (for example 7.80). As previously described, one of skill in the art will understand how to adjust the pH according to the desired pH measurements used in the reaction solution of the apparatus.

Figure 5A:
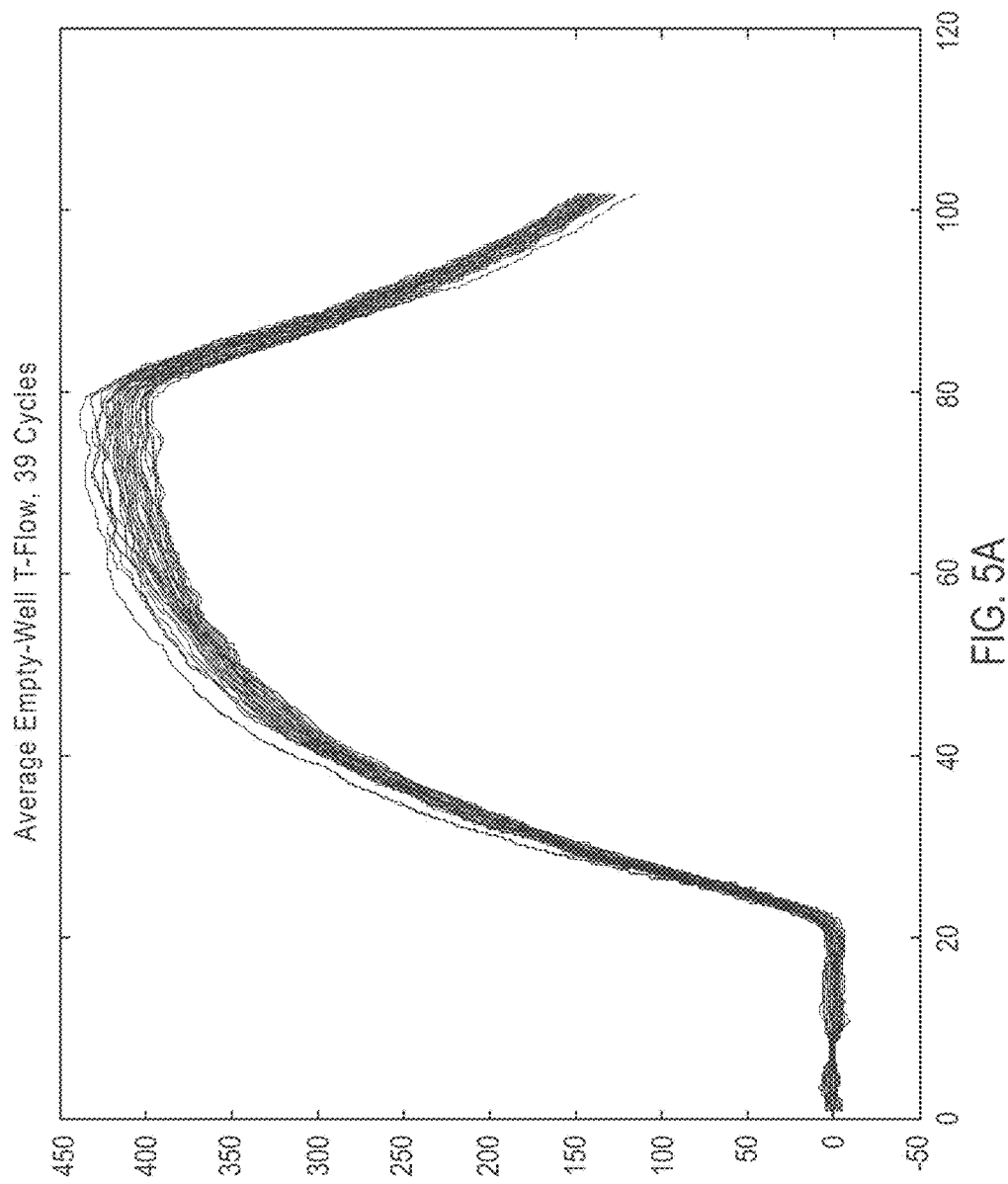
FIG. 5A illustrates the raw signal measured when a nucleotide was flowed across 39 cycles.
Figure 7:
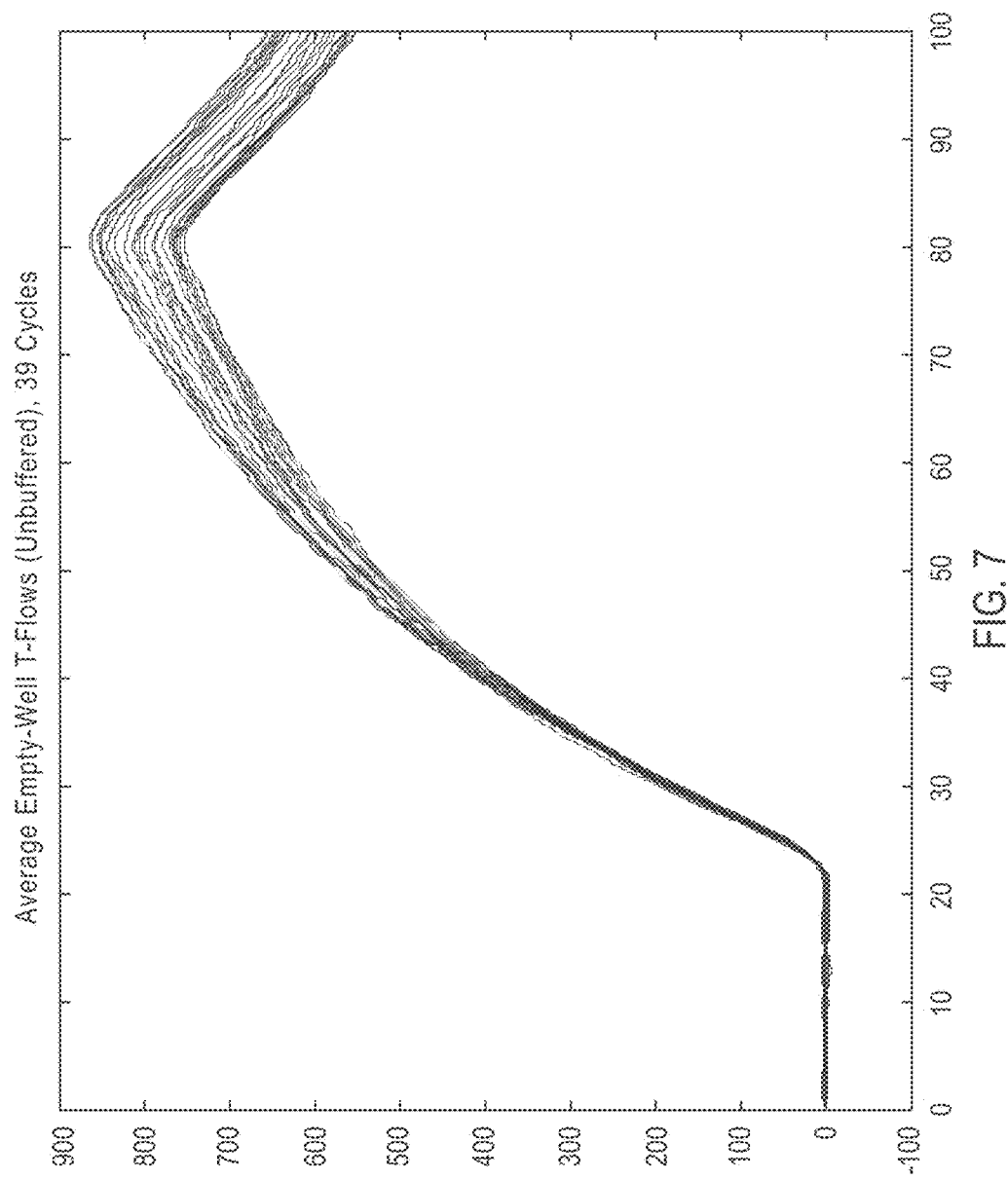
FIG. 7 illustrates the unbuffered signal measured when a nucleotide was flowed across 39 cycles.

Certain advantages can be realized from this implementation where the T nucleotide was flowed across 39 cycles, the results of which are depicted in FIG. 5A. Here, the immobilized buffer particles were able to hold the pH of the reagents more stably than would occur in an experiment without buffer particles. Additionally, the immobilized buffer particles were able to buffer the bulk pH change that occurred when the nucleotide was added. Additionally, the immobilized buffer particles were not increasing the rate at which protons transport in and out of the wells like a conventional buffer would. In one exemplary embodiment, the raw signal can be measured when a nucleotide, such as, for example, a T nucleotide, is flowed or allowed to flow across a certain number of cycles, such as, for example, across 39 cycles. See, FIG. 5A. Surprisingly, it can be found that there is very little drift in the amplitude of the pH step across the 39 cycles, for example. This indicates the immobilized buffer particles are holding the pH of the reagents more stable than an experiment without buffer particles could. In one aspect, the total amplitude is lower than is generally seen for a T flow, for example, lower than 800 counts or more (see FIG. 7 depicting measurements of unbuffered signal). This indicates that the immobilized buffer particles buffer the bulk pH change that occurs when nucleotide is added. By comparison, FIG. 7 depicts a typical T flow in an unbuffered experiment across 39 cycles. The amplitude of the pH change is at least two times that of the buffered experiment, and the variability in the pH change is at least two times as well. However, it should be noted that the T is not flowed for long enough to see the full equilibration to the total pH step amplitude.

In another embodiment, the rate of equilibration of the solution may be very similar to standard conditions, such as, for example, where the slope of the pH change looks very similar to a typical experiment. This indicates that the immobilized buffer particles are not increasing the rate at which protons transport between the confinement regions and the bulk fluid as a conventional buffer would.

Figure 5B:
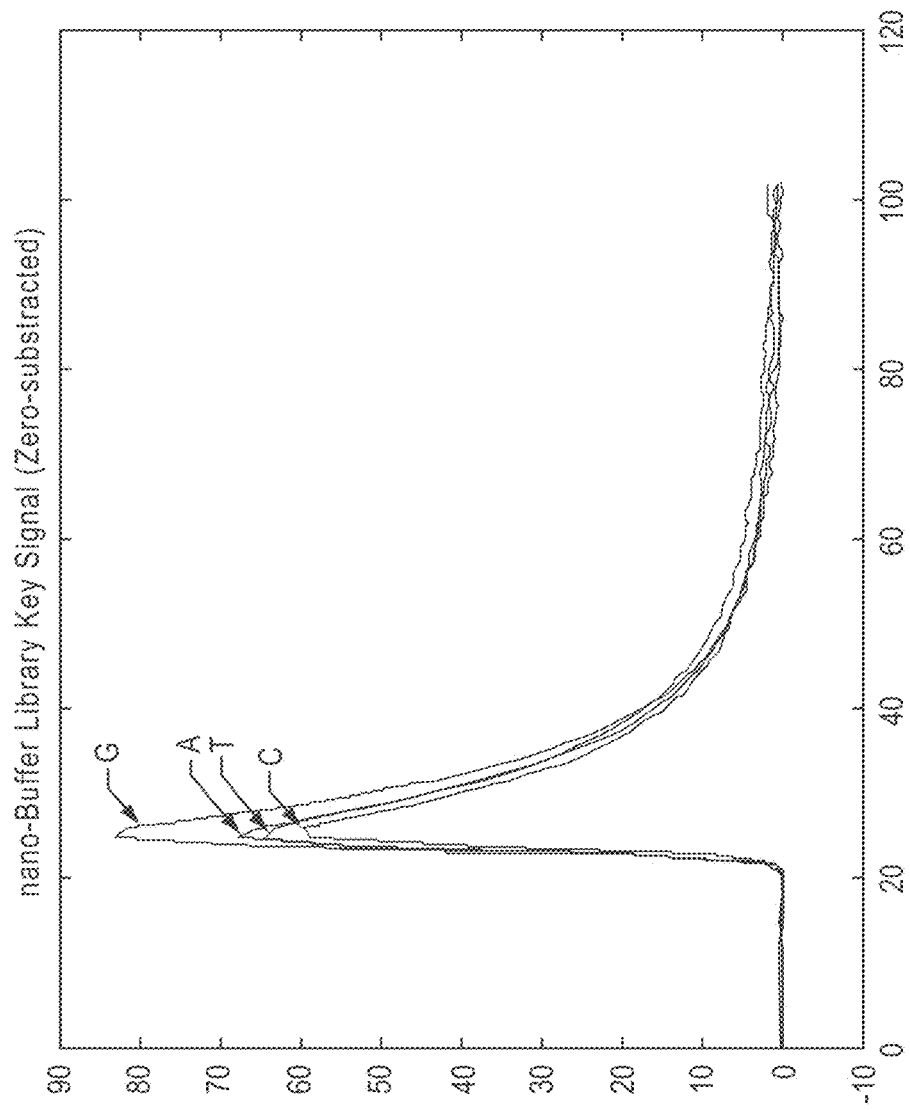
FIG. 5B illustrates the key signal data measured in one run for 4 nucleotides.

FIG. 5B: This figure depicts the average key incorporation measured in the same run for all 4 nucleotides. Here, the key signal amplitude and the decay rate of the signal are within expected and normal ranges. This indicates that the buffer is not affecting the transport of signal in and out of wells significantly.

Implementation 3: The buffering capacity and range can be adjusted as required. The buffering capacity was determined by the relative concentration of the buffering monomer (M) and the total solid components (% w/v). The buffering range can be expanded by using a second buffering monomer with appropriate pKa. For example, monomer (M) has a pKa of 8.03. If there is need to pull significantly more acidic solutions to the operating pH of 7.8, for example, a second buffering monomer such as, 2-(4-imidazolyl)ethylamine-2-acrylamide (IM), can be used, which has a pKa of 7.0. In this implementation the solid state buffer was a submicron sized hydrogel consisting of a 20% w/v random copolymer of 2-acrylamido-2-methyl-1-propane sulfonic acid sodium salt (S) (55% of total solids w/w), N-(3-morpholinopropyl)-acrylamide (M) (20% of total solids w/w), 2-(4-imidazolyl)ethylamine-2-acrylamide (IM) (20% of total solids w/w) and N-methylene bisacrylamide (BA) (5% of total solids w/w). A solution of the monomers in water was added to a heterophasic mixture that was subjected to ultrasonic agitation (horn sonicator at 50% max amplitude for 3+1+1 minutes). The resulting sub-micron emulsion was mixed with equal volume oil/surfactant mix that shortly before had been saturated with AIBN. The mixture was placed in a force air oven at 90 degrees Celsius for 2 hours under constant rotation. The polymerized nanospheres were recovered from the oil mixture and washed with appropriate surfactant solutions and finally activated by titration to an appropriate constant pH with sodium hydroxide solution (for example 7.80). The pH can be adjusted according to known methods in the art and as described previously in this disclosure. The three implementations above are all submicron sized particles which are suspended in all buffers and solutions during a sequencing run. Alternatively, the particles can be contained in a bag which allows the diffusion and convection of liquids across the bag lining but limits the particles to the interior of the bag. These bags may be placed in the reagent or buffer bottles/containers such that the solutions are buffered to the appropriate pH, but the solid state buffer is prevented from flowing through the tubing and flow cell.

In various exemplary embodiments, alternative configurations/strategies to having the particles suspended, such as, for example, in a hydrogel, may be used. By way of a non-limiting example, a polymer film with a similar composition to the buffering polymer particles can be grafted on the interior surfaces of tubing and/or flow cells. Here, the buffer can be reset by the W2 wash and is able to buffer differences in pH seen in nucleotide solutions minimizing background signal. Alternatively, a large molecular weight polymer with very slow diffusion time constants with a similar composition to the buffering polymer particles may be used, with the exception that the polymer would not be cross-linked. Still other strategies may be used as alternatives to the suspended particle configuration.

System for Nucleic Acid Sequencing

The compositions and apparatus of the disclosure are particularly useful in pH-based DNA sequencing. The concept of label-free DNA sequencing, including pH-based DNA sequencing, has been described in the literature, including the following references that are incorporated herein by reference: Rothbert et al., U.S. Patent Publication No. 2009/0026082; Anderson et al., *Sensors and Actuators B Chem.*, 129; 79-86 (2008); Pourmand et al., *Proc. Natl. Acad. Sci.*, 103; 6466-6470 (2006); and the like. Briefly, in general, in pH-based DNA sequencing, base incorporations are determined by measuring hydrogen ions that are generated as natural byproducts of polymerase-catalyzed extension reactions. In one embodiment, templates each having a primer and polymerase operably bound are loaded into confinement regions (such as the microwells disclosed in Rothbert et al., cited above), after which repeated cycles of deoxynucleoside triphosphate (dNTP) addition and washing are carried out. In some embodiments, such templates may be attached as clonal populations to a solid support, such as a microparticle, bead, or the like, and such clonal populations are loaded into confinement regions. For example, templates may be prepared as disclosed in U.S. Pat. No. 7,323,305, which is incorporated by reference. As used herein, "operably bound" means that a primer is annealed to a template so that the primer's 3' end may be extended by a polymerase and that a polymerase is bound to such primer-template duplex, or in close proximity thereof so that binding and/or extension takes place whenever dNTPs are added.

In each addition step of the cycle, the polymerase extends the primer by incorporation added dNTP only if the next base in the template is the complement of the added dNTP. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the confinement region. The production of hydrogen ions is monotonically related to the number of contiguous complementary bases in the template (as well as the total number of template molecules with primer and polymerase that participate in an extension reaction). Thus, when there is a number of contiguous identical complementary bases in the template (i.e. a homopolymer region), the number of hydrogen ions generated, and therefore the magnitude of the local pH change, is proportional to the number of contiguous identical complementary bases. (The corresponding output signals are sometimes referred to as "1-mer", "2-mer", "3-mer" output signals, and so on). If the next base in the template is not complementary to the added dNTP, then no incorporation occurs and no hydrogen ion is released (in which case, the output signal is sometimes referred to as a "0-mer" output signal.) In each wash step of the cycle, an unbuffered wash solution at a predetermined pH is used to remove the dNTP of the previous step in order to prevent misincorporations in later cycles. Usually the four different kinds of dNTP are added sequentially to the confinement regions, so that each reaction is exposed to the four different dNTPs one at a time, such as, for example, in the following sequence: dATP, dCTP, dGTP, dTTP, dATP, dCTP, dGTP, dTTP, and so on, with each exposure followed by a wash step.

The process is illustrated in FIG. 1 for template 182 with primer binding site 181 attached to solid phase support 180. Primer 184 and DNA polymerase 186 are operably bound to template 182. Upon the addition 188 of dNTP (shown as dATP), polymerase 186 incorporates a nucleotide since "T" is the next nucleotide in template 182 and produces hydrogen ion 100. Wash step 190 follows, after which the next dNTP (dCTP) 192 is added. Optionally, after each step of adding a dNTP, an additional step may be performed wherein the confinement regions are treated with a dNTP-destroying agent, such as, for example, apyrase, to eliminate any residual dNTPs remaining in the zones, which may result in spurious extensions in subsequent cycles.

In one embodiment, a sequencing method exemplified in FIG. 1 may proceed using the apparatus of the disclosure in the following steps: (a) disposing a plurality of template nucleic acids into a plurality of confinement regions disposed on a sensor array, the sensor array comprising a plurality of sensors and at least one confinement region being disposed on and in a sensing relationship with at least one sensor configured to provide at least one output signal representing a sequencing reaction byproduct proximate thereto, and wherein each of the template nucleic acids is hybridized to a sequencing primer and is bound to a polymerase; (b) introducing a known nucleotide triphosphate into the at least one confinement region; (c) detecting incorporation at a 3' end of the sequencing primer of one or more nucleotide triphosphates by a sequencing reaction byproduct if such one or more nucleotides triphosphates are complementary to corresponding nucleotides in the template nucleic acid; (d) washing unincorporated nucleotide triphosphates from the at least one confinement regions; and (e) repeating steps (b) through (d) until the plurality of template nucleic acids are sequenced.

When such reactions are carried out in an array of fluidly-connected confinement regions, a significant source of noise may arise when successive reagent flows pass over a sensor array (i.e., reagent change noise, also referred to herein as "drift" in pH). The magnitude of such noise depends on several factors including whether a leading or trailing reagent in a reagent change has a property or constituent, such as pH, which affects sensor performance and the magnitude of the influence, the relative magnitude of the reagent change effect in comparison with the reaction signal being monitored, and so on.

Figure 2A:
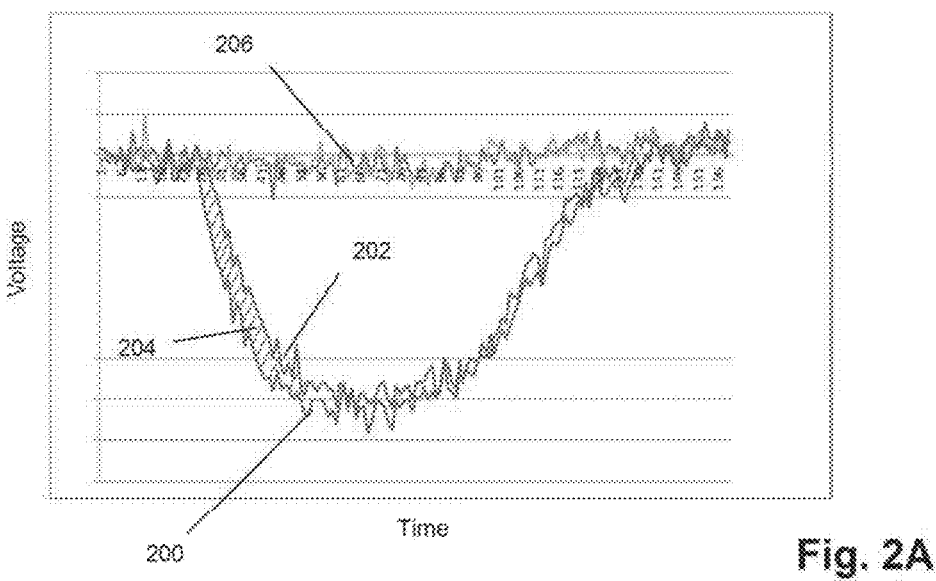
FIGS. 2A and 2B illustrate output signal data from a pH-sensitive electronic sensor of a microwell in which a pH-based sequencing reaction is taking place.

For pH-based DNA sequencing applications, for example, pH-sensitive sensors may generate a signal in response to a reagent change that is large in comparison to the signal due to hydrogen ion byproduct, as illustrated by the data of FIG. 2A. In such applications, different reagents, such as, for example, solutions containing different dNTPs, have slightly different buffering capacities and pKa's, so that at a boundary of different reagent flows, for example, a wash solution flow followed by a dNTP flow, the sensors register a significant voltage change, as illustrated in FIG. 2A.

Figure 2B:
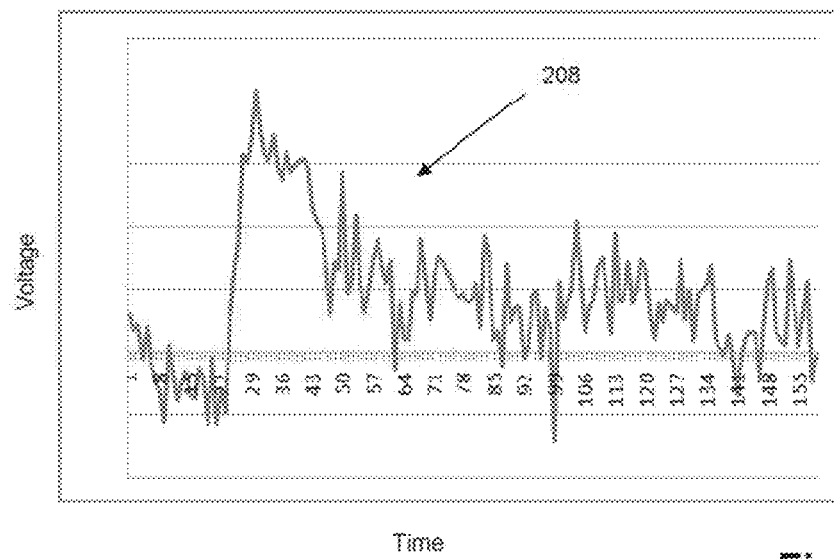

FIG. 2A shows the magnitudes of four output signals from different microwells of a DNA sequencing chip as disclosed is Rothberg et al., cited above, which employs conventional ion-sensitive field-effect transistor (ISFET) sensors. Curve 206 illustrates signals from microwells during a wash step with no changes in reagent. Curve 200 shows an output signal from a microwell containing a particle with template attached where a primer on the template has been extended by one nucleotide. Curve 202 is the output signal from a microwell that contains a particle with a template where there has been no extension. Region 204 is the difference between the two output signals (202 and 204) that is due to generation of hydrogen ion in the microwell where extension has taken place. Curve 208 in FIG. 2B, which is the difference between the values of curves 200 and 202, is the part of the raw output signal of curve 200 which is due to hydrogen ion produced in the extension reaction, i.e., the signal of interest. In accordance with the disclosure, such reagent change noise and other noise components common to local groups of microwells may be subtracted from an output signal of a selected sensor by using information from output signals generated from neighboring microwells.

Figure 6A:
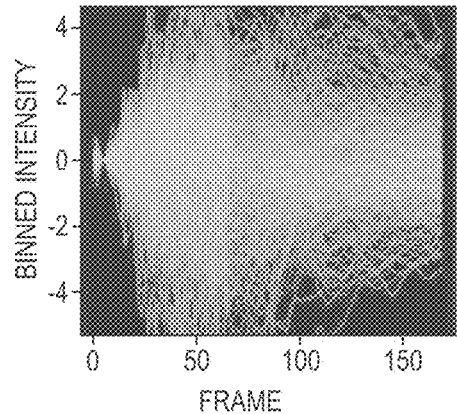
FIGS. 6A (control), 6B (10 um particle), 6C (12 um particle) illustrates output signal data from a pH-sensitive electronic sensor of an empty microwell.
Figure 6B:
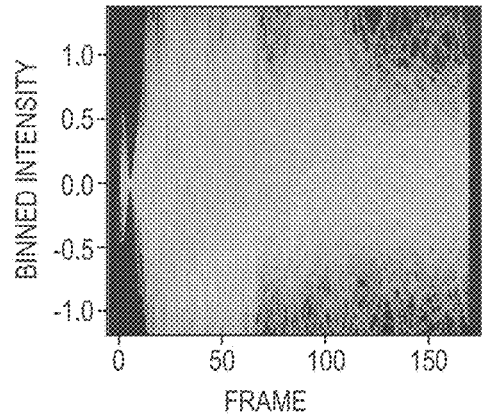
Figure 6C:
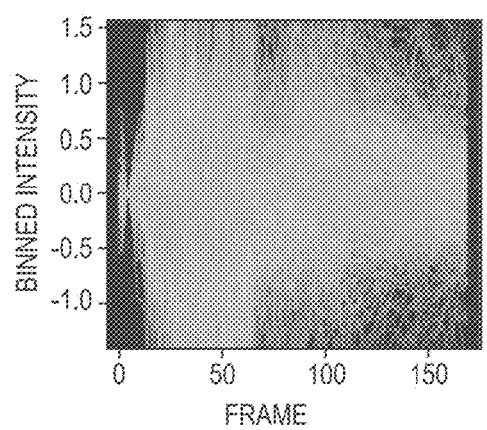

In one embodiment, such neighboring microwell information is obtained from at least one average value of output signals from one or more neighboring wells. In another embodiment, neighboring microwell information is obtained from output signals of empty wells, such as that depicted in FIGS. 6A (control), 6B (10 um particle), 6C (12 um particle). In still another embodiment, neighboring microwell information is obtained from output signals of non-empty microwells where no extension reaction took place. Correction of raw output signals by subtracting reagent change noise may be carried out after each reagent change based on averages computed after each such change, or such corrections may be carried out using averages computed from a previous reagent change, depending on the rate at which averages change during a multi-stop or multi-cycle electrochemical process. For example, in a DNA sequencing embodiment, an average may be computed for each different dNTP flow in a cycle (where a succession of the four different dNTPs is introduced into confinement regions) and used to correct raw output signals for from 1 to 5 cycles of reagent change.

In one aspect, compositions and apparatuses of the disclosure may be used to address the problem of reagent change noise, as illustrated by the diagram of FIG. 3A.

Figure 3:
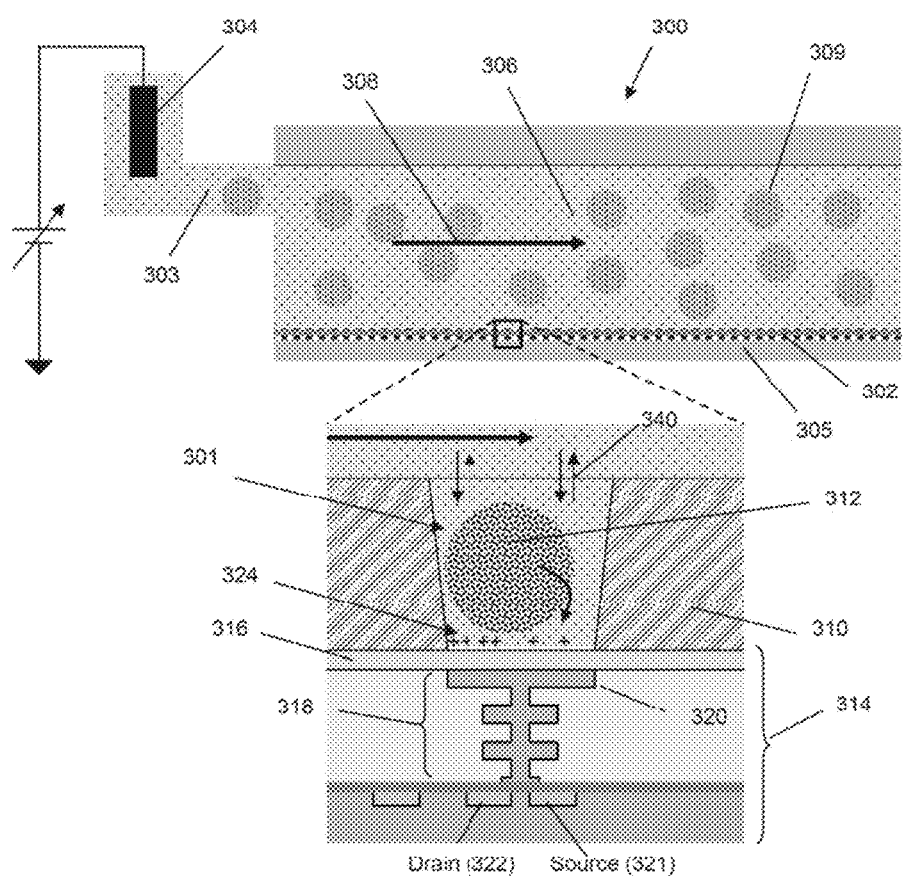
FIG. 3 illustrates a section of a flow cell with an external reference electrode and enlargement of an exemplary electronic sensor.

FIG. 3 is an expanded and cross-sectional view of flow cell 200, which comprises an inlet, an outlet, and a flow chamber, which includes a microwell array with associated electronic pH sensors. FIG. 3 shows a portion 306 of a flow chamber with reagent 308 moving across the surface of microwell array 302 over the open ends of the microwells.

Mixed with reagent 308 are immobilized buffer particles 309. Preferably, microwell array 302 and sensor array 305 together form an integrated unit forming a bottom wall or floor of flow cell 300. In one embodiment, reference electrode 304 is fluidly connected to flow chamber 306. A microwell 301 and sensor 314 are shown in an expanded view. Microwell (301) may be formed by conventional microfabrication technique, as described briefly below. Microwell volume, shape, aspect ratio (such as, base width-to-well depth ratio), and the like, are design choices that depend on a particular application, including the nature of the reaction taking place, as well as the reagents, byproducts, and labeling techniques (if any) that are employed. Sensor 314 is a chemFET with floating gate 318 having sensor plate 320 separated from the microwell interior by passivation layer 316. Sensor 314 is predominantly responsive to (and generates an output signal related to) the amount of charge 324 cause changes in the current between source 321 and drain 322 of the FET, which may be used directly to provide a current-based output signal or indirectly with additional circuitry to provide a voltage output signal. Sensor 314 is able to detect other properties and produce output signals for those properties in addition to measuring hydrogen ion presence. For example, the sensor may be able to measure heat within the apparatus from the reactions or measure phosphate levels within the apparatus. Importantly, as can be understood by one of skill in the art, there are many properties that can be measured within the apparatus or as part of a mixture, solution or reaction. Those listed here are only a few of those that can alter the pH measurements and are not meant to be all inclusive or limiting examples. Reactants, wash solutions, and other reagents move into microwells from flow chamber 306 primarily by diffusion 340.

Figure 4:
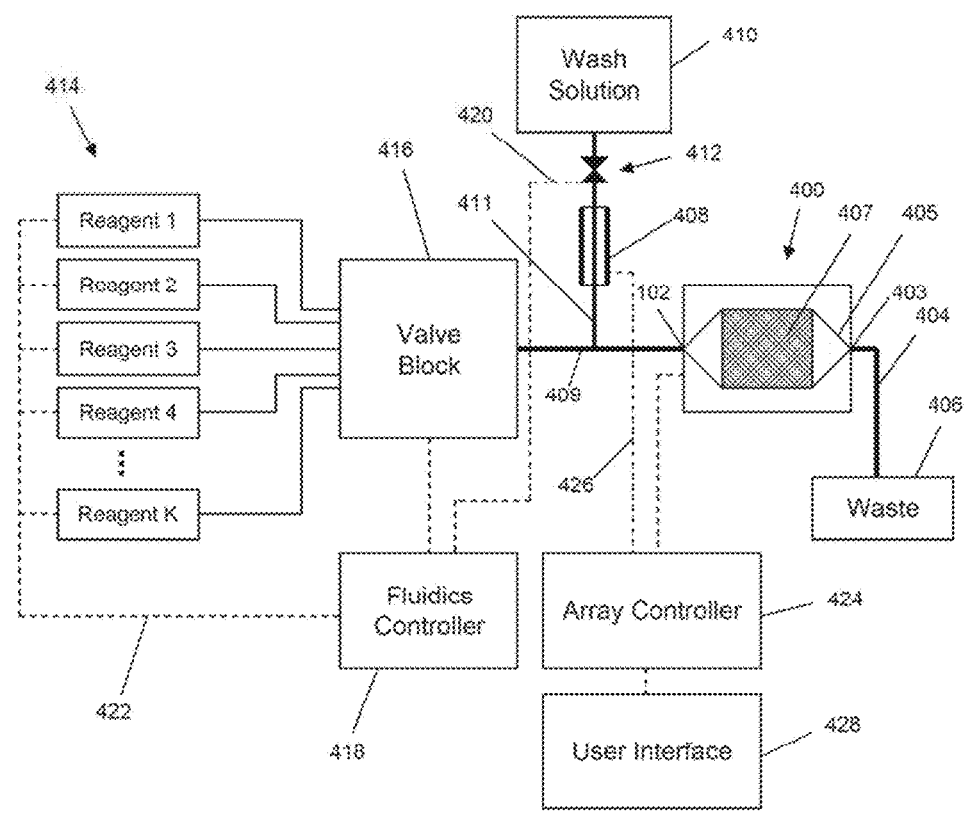
FIG. 4 illustrates components of an instrument for carrying out a pH-based DNA sequencing method.

Components of an instrument for performing pH-based DNA sequencing in connection with the disclosure are illustrated diagrammatically in FIG. 4. Flow cell and sensor array 400 comprise an array of reaction confinement regions, which may comprise a microwell array, which is operationally associated with a sensor array, so that, for example, each microwell has a sensor suitable for detecting an analyte or reaction property of interest. Preferably, a microwell array is integrated with the sensor array as a single chip, as explained more fully below. A flow cell can have a variety of designs for controlling the path and flow rate of reagents over the microwell array. In some embodiments, a flow cell is a microfluidic device. That is, it may be fabricated with micromachining techniques or precision molding to include additional fluidic passages, chambers, and so on. In one aspect, a flow cell comprises an inlet 402, an outlet 403, and a flow chamber 405 for defining the flow path of reagents over the microwell array 407. Embodiments of the flow cell are described more fully below. Reagents are discarded into waste container 406 after exiting flow cell and sensor array 400. In accordance with the disclosure, a function of the apparatus is to deliver different reagents to flow cell and sensor array 400 in a predetermined sequence, for predetermined durations, at predetermined flow rates, and to measure physical and/or chemical parameters in the microwells that provide information about the status of a reaction taking place therein, or in the case of empty wells, information about the physical and/or chemical environment in the flow cell. To this end, fluidics controller 418 controls by lines 420 and 422 the driving forces for a plurality of reagents 414 and the operation of valves, for example, 412 and 416, by conventional instrument control software, e.g., LabView (National Instruments, Austin, Tex.). The reagents may be driven through the fluid pathways, valves and flow cell pumps, by gas pressure, or other conventional methods. In embodiments where a single reference electrode 408 is positioned upstream of flow cell and sensor array 400, preferably a single fluid or reagent is in contact with reference electrode 408 throughout an entire multi-step reaction. This is achieved with the configuration illustrated in FIG. 4 where reagents 1 through K 414 are directed through passage 409 to flow cell 405. When those reagents are flowing, valve 412 is shut, thereby preventing any wash solution from flowing into passage 409. Although the flow of wash solution is stopped, there is still uninterrupted fluid and electrical communication between reference electrode, passage 409, and sensor array 407. At most reagents 1 through K when flowing through passage 409 diffuse into passage 411, but the distance between reference electrode 408 and the junction between passages 409 and 411 is selected so that little or no amount of the reagents flowing in common passage 409 reach reference electrode 408. Although FIG. 4 and other figures illustrate an electrode, for example, reference electrode 408, as a cylinder concentric with a fluid passage 411, for example, reference electrodes, such as 408, may have a variety of different shapes. For example, it could be a wire inserted into the lumen of 411. In one aspect, reference electrode 408 constitutes a section of passage 412 that is made of a conductive material, such as stainless steel, gold, or the like. Preferably the material is inert with respect to reagents in contact with it. Reference electrode 408 in one embodiment, is a tube made of a conductive material which forms part of passage 412. Generally in the figures, whenever electrodes are represented as a cylinder concentric with a flow path, such figure element is intended to comprise electrodes having a variety of configurations, as noted, but with a preferred configuration as a tube of conductive material enclosing part of a flow path.

The value of the reference voltage depends on the interface between the electrode and the solution in which the electrode is in contact. It has been observed and appreciated that solutions of different nucleoside triphosphates, for example, cause the reference voltage to change, thereby causing undesirable changes in the output signals of the sensors. For multi-step reactions using frequent wash steps, wash solution 410 may be selected as the reagent in continuous contact with reference electrode 408 as illustrated in FIG. 4. For example, the wash solution would be the "selected electrolyte" or "selected reagent" and the dNTP reagents would be the "non-selected electrolytes" or "non-selected reagents" as the terms used throughout this disclosure. As further described below, in certain DNA sequencing methods, washes are implemented after each introduction of nucleoside triphosphates; thus, in such methods, a wash solution is preferably in continuous contact with reference electrode 408. Such contact may be obtained by including a reservoir for holding the selected electrolyte, such as the wash solution, which is connected by a branch passage, e.g., 411, to a common passage, e.g., 409, for delivering electrolytes to a reaction to a reaction vessel. In one aspect, the branch passage has a valve disposed between the reservoir, e.g., 410, and a junction with the common passage, wherein the reference electrode is disposed in the branch passage between the valve and the junction such that the reference electrode is in fluid communication with the reaction vessel and such that whenever the valve, e.g., 412, is shut and fluid within the branch passage is stationary, substantially no non-selected electrolyte contacts the reference electrode. The only transfer of non-selected electrolyte in the branch passage is by diffusion; thus, the reference electrode may be place sufficiently far away from the junction so that minimal or no non-selected electrolyte reaches it during the time the selected electrolyte is stationary.

Further components of this embodiment include array controller 424 for providing bias voltages and timing and control signals to the sensor array, if such components are not integrated into the sensor array, and for collecting and/or processing output signals. Information from flow and sensor array 400, as well as instrument settings and controls, may be displayed and entered through user interface 428. For some embodiments, for example, nucleic acid sequencing, the temperature of flow cell and sensor array 40 is controlled so that reactions take place and measurements are made at a known, and preferably, a predetermined temperature. Such temperature may be controlled by conventional temperature control devices, such as, a Peltier device, or the like. In one aspect, temperature is conveniently controlled by controlling the temperature of reagents flowing through the flow cell. Noise in output signals due to temperature differences within an array or due to temperature fluctuations may be recorded by temperature reference sensors within the array, as described in Rothberg et al. (published patent application cited above). Such noise may then be subtracted from the output signal in conventional signal processing techniques.

Definitions

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, for example, to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, such as, having maximal cross-sectional dimensions of from about 500 um to about 0.1 um. Microfluidics devices typically have volume capacities in the range of from 1 uL to a few nL, for example, 10 to 100 nL. The fabrication and operation of microfluidics devices are well-known in the art as exemplified by the following references that are incorporated herein by reference: Ramsey, U.S. Pat. Nos. 6,001,229; 5,858,195; 6,010,607; and 6,033,546; Soane et al., U.S. Pat. Nos. 5,126,022 and 6,054,034; Nelson et al., U.S. Pat. No. 6,613,525; Maher et al., U.S. Pat. No. 6,399,952; Ricco et al., International Patent Publication No. WO 02124322; Bjornson et al., International Patent Publication No. WO 99119717; Wilding et al., U.S. Pat. Nos. 5,587,128; 5,498, 392; Sia et al., *Electrophoresis*, 24: 3563-3576 (2003); Unger et al., *Science*, 288: 113-116 (2000); Enzelberger et al., U.S. Pat. No. 6,960,437.

"Microwell," refers to a particular type of "confinement region," "reaction chamber," or the like, that is, a physical or chemical attribute of a solid substrate that permits the localization of a reaction of interest. Confinement regions in or on which reactions may occur may be discrete regions of a surface of a substrate that specifically binds an analyte of interest, such as a discrete region with oligonucleotides or antibodies covalently linked to such surface. Usually reaction confinement regions are hollows or wells having well-defined shapes and volumes, which are manufactured into a substrate. These latter types of reaction confinement regions are referred to herein as microwells or confinement regions, and may be fabricated using conventional microfabrication techniques, such as those disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al., Silicon Micromachining (Cambridge University Press, 2004); and the like. Preferable configurations (e.g., spacing, shape and volumes) of microwells or confinement regions are disclosed in Rothberg et al., U.S. Patent Publication No. 2009/0127589; and Rothberg et al., U.K. Patent Application No. G824611127, which are incorporated herein by reference. Microwells may have square, rectangular, or octagonal cross sections and be arranged as a rectilinear array on a surface. Microwells may also have hexagonal cross sections and be arranged as a hexagonal array, which permit a higher density of microwells per unit area in comparison to rectilinear arrays. Exemplary configurations of microwells are as follows: In some embodiments, the array of confinement regions comprises $10^2$, $10^3$, $10^4$, $10^5$, $10^6$ or $10^7$ confinement regions. As used herein, an array is a planar arrangement of elements such as sensors or wells. The array may be one or two-dimensional. A one-dimensional array is an array having one column (or row) of elements in the first dimension and a plurality of columns (or rows) in the second dimension. The number of columns (or rows) in the first and second dimensions may or may not be the same. Preferably, the array comprises at least 100,000 confinement regions. Preferably, each confinement region has a horizontal width and a vertical depth that has an aspect ratio of about 1:1 or less. Preferably, the pitch between the confinement regions is no more than about 10 microns.

Briefly, in one embodiment, microwell arrays may be fabricated as follows: After the semiconductor structures of a sensor array are formed, the microwell structure is applied to such structure on the semiconductor die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as, Microchem's SU-8 2015 or a positive resist/polyimide such as HD Microsystems HD8820, to the desired height of the microwells. The desired height of the wells (e.g., about 3-12 um in the example of one pixel per well, though not so limited as a general matter) in the photoresist layer(s) can be achieved by spinning the appropriate resist at predetermined rates, which can be found by reference to the literature and manufacturer specifications, or empirically, in one or more layers. Well height typically may be selected in correspondence with the lateral dimension of the sensor pixel, preferably for a nominal 1:1-1.5:1 aspect ratio, height:width or diameter.

Alternatively, multiple layers of different photoresists may be applied or another form of dielectric material may be deposited. Various types of chemical vapor deposition may also be used to build up a layer of materials suitable for microwell formation therein. In one embodiment, microwells are formed in a layer of tetra-methyl-ortho-silicate (TEOS). The disclosure encompasses an apparatus comprising at least one two-dimensional array of confinement regions, wherein each confinement region is coupled to a chemically-sensitive field effect transistor ("chemFET") and at least one confinement region is no greater than 10 um (i.e., 1 pL) in volume. In some embodiments, each confinement region is no greater than 0.34 pL, and more preferably no greater than 0.096 pL or even 0.012 pL in volume. A confinement region can optionally be $2^2$, $3^2$, $4^2$, $5^2$, $6^2$, $7^2$, $8^2$, $9^2$, or $10^2$ square microns in cross-sectional area at the top. Preferably, the array has at least $10^2$, $10^3$, $10^4$, $10^5$, $10^6$, $10^7$, $10^8$, $10^9$, or more confinement regions. The confinement regions may be capacitively coupled to the chemFETs, and preferably are capacitively coupled to the chemFETs.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well-known to those of ordinary skill in the art, as evidenced by the following references that are incorporated by reference: Dieffenbach, editor, *PCR Primer: A Laboratory Manual*, 2nd Edition (Cold Spring Harbor Press, New York, 2003).

What is claimed is:

1. A method for sequencing, the method comprising:
   disposing a plurality of support particles including template nucleic acids into a plurality of confinement regions, a confinement region of the plurality of confinement regions in sensing relationship with a sensor of a sensor array, the sensor configured to provide at least one output signal representing a sequencing reaction byproduct, each confinement region of the plurality of confinement regions having an opening exposed to a flow chamber;
   flowing through the flow chamber a reagent solution including buffer particles incorporating immobilized buffering groups, the buffer particle being in spatial relation to the plurality of confinement regions to buffer a solution without substantially buffering the plurality of confinement regions in which the plurality of template nucleic acids are disposed;
   introducing a nucleotide through the flow chamber and into the confinement region; and
   detecting an incorporation of the nucleotide onto a template nucleic acid of the plurality of template nucleic acids.

2. The method of claim 1, wherein the buffer particles include a hydrophilic polymer.

3. The method of claim 2, wherein the hydrophilic polymer includes polyacrylamide.

4. The method of claim 1, wherein the buffer particles include one or more of the immobilized buffering groups selected from the group consisting of triethanolamine, N-[tris(hydroxymethyl) methyl]-2-aminoethanesulfonic acid, 3-(N-tris[hydroxymethyl]methylamino)-2-hydroxypropanesulfonic acid, N-(2-hydroxyethyl)piperazine-N-(2-ethanesulfonic acid), N-(2-acetamido)-2-aminoethanesulfonic acid, imidazole, and acetate.

5. The method of claim 4, wherein the one or more buffering groups have a pKa within the range of about 4.5 to about 9.0.

6. The method of claim 5, wherein the pKa in the range of about 6.0 to about 8.0.

7. The method of claim 1, further comprising applying a buffer particle to another confinement region different from the plurality of confinement regions in which the plurality of template nucleic acids are disposed.

8. The method of claim 1, wherein the buffer particles have a size larger than the plurality of confinement regions.

9. The method of claim 1, wherein the buffer particles have a diameter in a range from 0.5 micrometers to 100 micrometers.

10. The method of claim 1, wherein the buffer particles further include an avidin moiety or a biotin moiety.

11. A method of sensing a characteristic of a polynucleotide with a sensor array, the method comprising:
    disposing the polynucleotide in a confinement region in sensing relationship to a sensor of the sensor array, the sensor responsive to pH change within the confinement region, the confinement region having an opening exposed to a flow chamber;
    applying a reagent solution including an immobilized buffer particle to the flow chamber, a reagent of the reagent solution entering the confinement region, the immobilized buffer particle buffering the reagent solution in the flow chamber outside of the confinement region, the confinement region remaining substantially unbuffered; and
    detecting a pH change within the confinement region indicative of the characteristic of the polynucleotide.

12. The method of claim 11, wherein the immobilized buffer particle includes a hydrophilic polymer.

13. The method of claim 12, wherein the hydrophilic polymer includes polyacrylamide.

14. The method of claim 11, wherein the immobilized buffer particle includes one or more buffering groups selected from the group consisting of triethanolamine, N-[tris(hydroxymethyl) methyl]-2-aminoethanesulfonic acid, 3-(N-tris[hydroxymethyl]methylamino)-2-hydroxypropanesulfonic acid, N-(2-hydroxyethyl)piperazine-N-(2-ethanesulfonic acid), N-(2-acetamido)-2-aminoethanesulfonic acid, imidazole, and acetate.

15. The method of claim 14, wherein the one or more buffering groups have a pKa within the range of about 4.5 to about 9.0.

16. The method of claim 15, wherein the pKa in the range of about 6.0 to about 8.0.

17. The method of claim 11, further comprising applying the immobilized buffer particle to another confinement region different from confinement regions in which the polynucleotide is disposed.

18. The method of claim 11, wherein the immobilized buffer particle has a size larger than the plurality of confinement regions.

19. The method of claim 11, wherein the immobilized buffer particle further includes an avidin moiety or a biotin moiety.

20. The method of claim 11, wherein the immobilized buffer particle has a diameter in a range from 0.5 micrometers to 100 micrometers.

* * * * *